United States Patent
Nakajima et al.

(10) Patent No.: US 9,341,544 B2
(45) Date of Patent: May 17, 2016

(54) ABNORMALITY DETECTING DEVICE OF INTERNAL COMBUSTION ENGINE

(71) Applicants: Isao Nakajima, Nisshin (JP); Yoshifumi Matsuda, Toyota (JP); Yoshihisa Oda, Toyota (JP); Masashi Hakariya, Nagoya (JP); Masahide Okada, Anjou (JP); Hiroaki Tsuji, Miyoshi (JP); Tokiji Ito, Toyota (JP); Tatsuro Shimada, Toyota (JP); Toshihiro Kato, Toyota (JP); Yuya Yoshikawa, Chiryu (JP)

(72) Inventors: Isao Nakajima, Nisshin (JP); Yoshifumi Matsuda, Toyota (JP); Yoshihisa Oda, Toyota (JP); Masashi Hakariya, Nagoya (JP); Masahide Okada, Anjou (JP); Hiroaki Tsuji, Miyoshi (JP); Tokiji Ito, Toyota (JP); Tatsuro Shimada, Toyota (JP); Toshihiro Kato, Toyota (JP); Yuya Yoshikawa, Chiryu (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 191 days.

(21) Appl. No.: 14/216,004

(22) Filed: Mar. 17, 2014

(65) Prior Publication Data

US 2014/0290348 A1  Oct. 2, 2014

(30) Foreign Application Priority Data

Mar. 27, 2013  (JP) .................................. 2013-067210

(51) Int. Cl.
   *G01M 15/10*   (2006.01)
   *F01N 11/00*   (2006.01)
   (Continued)

(52) U.S. Cl.
   CPC ......... *G01M 15/102* (2013.01); *F02D 41/1495* (2013.01); *F01N 11/00* (2013.01); *F01N 11/007* (2013.01); *F02D 41/1454* (2013.01);
   (Continued)

(58) Field of Classification Search
   CPC ............ F02D 41/1495; F02D 41/1441; F02D 41/1454; F02D 41/222; F02D 41/22; F02D 41/18; Y02T 10/47; Y02T 10/42; Y02T 10/44; F01N 11/00; F01N 11/007; G01M 15/102; G01M 15/104; G01M 15/10; G01N 1/2252
   USPC .............................. 73/114.71–114.73, 114.75
   See application file for complete search history.

(56) References Cited

U.S. PATENT DOCUMENTS 5,423,203 A * 6/1995 Namiki ............... F02D 41/1495
                                                  123/688
5,610,321 A * 3/1997 Shinmoto ........... F02D 41/1441
                                                  60/277

(Continued)

FOREIGN PATENT DOCUMENTS

JP   2003-014683 A   1/2003
JP   2004-225684 A   8/2004

(Continued)

*Primary Examiner* — Lisa Caputo
*Assistant Examiner* — Jonathan Dunlap
(74) *Attorney, Agent, or Firm* — Dinsmore & Shohl LLP

(57) ABSTRACT

An abnormality detecting device of an internal combustion engine according to the present invention includes a sensor nick abnormality detecting unit configured to detect a nick abnormality in a detecting element of a downstream side sensor which is provided in a downstream side of an exhaust gas purifying catalyst in an exhaust passage and generates an output corresponding to an oxygen concentration in exhaust gas, on the basis of a matter that a distribution of an output of the downstream side sensor is biased to an area in which the air-fuel ratio is leaner than a theoretical air-fuel ratio, and an inhibiting unit configured to inhibit detection of the nick abnormality of the detecting element by the sensor nick abnormality detecting unit in the case that an intake air amount exceeds a predetermined amount.

5 Claims, 16 Drawing Sheets

(51) Int. Cl.
G01N 1/22 (2006.01)
F02D 41/22 (2006.01)
F02D 41/14 (2006.01)
F02D 41/18 (2006.01)

(52) U.S. Cl.
CPC ............... *F02D41/18* (2013.01); *F02D 41/22* (2013.01); *F02D 41/222* (2013.01); *G01M 15/10* (2013.01); *G01M 15/104* (2013.01); *G01N 1/2252* (2013.01); *Y02T 10/42* (2013.01); *Y02T 10/44* (2013.01); *Y02T 10/47* (2013.01)

(56) References Cited

U.S. PATENT DOCUMENTS

| | | | | |
|---|---|---|---|---|
| 5,845,489 A * | 12/1998 | Dohta | ............... | F01N 11/00 123/688 |
| 6,374,818 B2 * | 4/2002 | Shinjyo | ............... | F02D 41/1441 123/198 D |
| 6,836,722 B2 * | 12/2004 | Yook | ............... | F02D 41/0295 60/274 |
| 6,920,751 B2 * | 7/2005 | Yasui | ............... | F02D 41/1441 60/274 |
| 7,900,616 B2 * | 3/2011 | Saunders | ............... | F02D 41/1454 123/688 |
| 8,670,917 B2 * | 3/2014 | Aoki | ............... | F02D 41/1454 123/673 |
| 8,744,729 B2 * | 6/2014 | Iwazaki | ............... | F02D 41/0085 123/673 |
| 8,776,586 B2 * | 7/2014 | Takagi | ............... | F01N 3/2013 73/114.73 |
| 2003/0005746 A1 | 1/2003 | Iwazaki et al. | | |
| 2004/0261498 A1 * | 12/2004 | Hattori | ............... | F02D 41/042 73/23.32 |
| 2009/0089011 A1 | 4/2009 | Iwazaki et al. | | |
| 2012/0323466 A1 | 12/2012 | Iwazaki et al. | | |
| 2013/0144510 A1 | 6/2013 | Iwazaki et al. | | |
| 2013/0291630 A1 * | 11/2013 | Takagi | ............... | F01N 3/2013 73/114.75 |
| 2014/0260533 A1 * | 9/2014 | Mintah | ............... | F02D 41/1461 73/23.31 |

FOREIGN PATENT DOCUMENTS

| | | |
|---|---|---|
| JP | 2005-337139 A | 12/2005 |
| JP | 2008-014670 A | 1/2008 |
| JP | 2009-281328 A | 12/2009 |
| WO | 2011070688 A1 | 6/2011 |
| WO | 2011155073 A1 | 12/2011 |

\* cited by examiner

ABNORMALITY DETECTING DEVICE OF INTERNAL COMBUSTION ENGINE

CROSS-REFERENCES TO RELATED APPLICATIONS

This application claims the benefit of Japanese Patent Application No. 2013-067210, filed Mar. 27, 2013, which is hereby incorporated by reference herein in its entirety.

BACKGROUND OF THE INVENTION

1. Field of the Invention

The present invention relates to an abnormality detecting device of an internal combustion engine including in an exhaust passage a sensor generating an output corresponding to an oxygen concentration in exhaust gas.

2. Description of the Related Art

Generally, in the internal combustion engine provided with an exhaust gas purifying system utilizing a catalyst, in order to efficiently carry out purification of harmful component in the exhaust gas by the catalyst, it is indispensable to control a mixing rate between air and fuel, that is, an air-fuel ratio in an air-fuel mixture burned in the internal combustion engine. In order to control the air-fuel ratio, in the internal combustion engine mentioned above, sensors each generating an output corresponding to the oxygen concentration in the exhaust gas are provided on upstream and downstream sides of an exhaust gas purifying catalyst, that is, a catalyst purifying device, in the exhaust passage, and an air-fuel ratio feedback control is carried out so as to make the air-fuel ratio detected by the sensors follow a predetermined target air-fuel ratio. For example, a wide area air-fuel ratio sensor is provided on the upstream side of the catalyst, and an oxygen sensor is provided on the downstream side thereof.

However, there is a case that a nick is generated in such the sensors, and the above-mentioned air-fuel ratio control cannot be appropriately carried out. Accordingly, in such a case, it is required to rapidly detect the nick and take a countermeasure such as repair.

Japanese Patent Laid-Open No. 2003-14683 discloses an abnormality diagnosing device of an oxygen sensor. A general oxygen sensor is disposed in an exhaust passage so as to expose an inner surface of its detecting element to an atmosphere and to expose an outer surface thereof to exhaust gas, and generates an electromotive force when a difference is generated in an oxygen partial pressure, that is, an oxygen concentration between the atmosphere and the exhaust gas, since an oxygen ion flows through the inner portion of the detecting element from a higher oxygen concentration side to a lower oxygen concentration side. However, if the nick is generated in the detecting element of the oxygen sensor, that is, if an element crack is generated, the exhaust gas flows into the inner portion of the detecting element, so that no difference is generated in the oxygen concentrations between the inner and outer sides of the detecting element. As a result, the oxygen sensor generates the same output as that during a so-called lean combustion time in which the oxygen is rich in the exhaust gas. In other words, if the nick is generated in the detecting element, possibility that the oxygen sensor generates the same output as that during the lean combustion time is increased. Accordingly, the device of Japanese Patent Laid-Open No. 2003-14683 pays attention to this phenomenon, and has a configuration which detects a nick abnormality in the detecting element of the oxygen sensor, on the basis of an output pattern of the oxygen sensor.

On the other hand, in an internal combustion engine having a plurality of cylinders, that is, a so-called multi-cylinder internal combustion engine, since an air-fuel ratio control is generally carried out by using the same control amount with respect to all the cylinders, the actual air-fuel ratio may vary between the cylinders, even by carrying out the air-fuel ratio control. If the variation degree is small at this time, the variation can be absorbed by an air-fuel ratio feedback control. Further, since the catalyst can also purify the harmful component in the exhaust gas, an exhaust emission is not affected, and any particular problem is not generated.

However, in the case that the air-fuel ratio between the cylinders greatly varies, for example, due to a failure of a fuel injection system or a valve system of an intake valve in one or some of the cylinders, and the exhaust emission is deteriorated, which causes a problem. It is desirable to detect such a great air-fuel ratio variation that deteriorates the exhaust emission as an abnormality.

For example, it is possible to detect the generation of the air-fuel ratio variation abnormality between the cylinders, by comparing a detected air-fuel ratio change rate based on the output of the wide area air-fuel ratio sensor provided in the exhaust passage with a threshold value for determination (refer, for example, to WO2011/070688).

SUMMARY OF THE INVENTION

There is supposed an internal combustion engine in which a wide area air-fuel ratio sensor is provided on an upstream side of a catalyst in an exhaust passage, and an oxygen sensor is provided on a downstream side thereof. In the internal combustion engine, as is mentioned in detail later, the oxygen sensor tends to generate an output as that during a lean combustion time, for example, due to an influence of a hydrogen component generated in an abnormal cylinder, in the case that the air-fuel ratio variation between the cylinders is great, and such the output tends to be generated particularly in the case that an intake air amount is large. Therefore, in the case that the internal combustion engine is provided with the configuration mentioned above for detecting the nick abnormality of the oxygen sensor, there is a possibility of an erroneous detection that the nick abnormality exists in the detecting element of the oxygen sensor as mentioned above, on the basis of the output of the oxygen sensor when the air-fuel ratio variation between the cylinders is great even without such the nick abnormality.

Accordingly, the present invention was made by taking the above circumstances into consideration, and has an object to prevent an erroneous detection that a nick abnormality exists in a sensor which generates an output corresponding to an oxygen concentration in exhaust gas, on the basis of the output of the sensor, in the case that an air-fuel ratio variation between cylinders is great.

According to an aspect of the present invention, there is provided an abnormality detecting device of an internal combustion engine comprising: a sensor nick abnormality detecting unit configured to detect a nick abnormality of a detecting element of a downstream side sensor which is provided in a downstream side of an exhaust gas purifying catalyst in an exhaust passage of an internal combustion engine having a plurality of cylinders and generates an output corresponding to an oxygen concentration in exhaust gas, on the basis of an output of the downstream side sensor, the sensor nick abnormality detecting unit detecting the nick abnormality in the detecting element of the downstream side sensor on the basis of a matter that a distribution of the output of the downstream side sensor is biased to an area in which the air-fuel ratio is leaner than a theoretical air-fuel ratio; and an inhibiting unit configured to inhibit detection of the nick abnormality of the detecting element by the sensor nick abnormality detecting unit in the case that an intake air amount exceeds a predetermined amount.

Preferably, the sensor nick abnormality detecting unit acquires an output voltage of the downstream side sensor a predetermined number of times, and determines a distribution of the output of the downstream side sensor on the basis of a number of times that the acquired output voltage is included in a predetermined voltage area. Further, the sensor nick abnormality detecting unit preferably detects the nick abnormality of the detecting element of the downstream side sensor on the basis of the output of the downstream side sensor in the case that an air-fuel ratio feedback stoichiometric control is carried out.

Preferably, there are further provided a value calculating unit which calculates a value indicating a degree of air-fuel ratio variation between the cylinders on the basis of an output of an upstream side air-fuel ratio sensor provided on an upstream side of the exhaust gas purifying catalyst, and a predetermined amount calculating unit which calculates the predetermined amount in the inhibiting unit on the basis of the value calculated by the value calculating unit.

Preferably, in the abnormality detecting device of the internal combustion engine or modification thereof, there are further provided a value calculating unit which calculates a value indicating a degree of air-fuel ratio variation between the cylinders on the basis of an output of an upstream side air-fuel ratio sensor provided on an upstream side of the exhaust gas purifying catalyst, a variation level detecting unit which detects that the degree of the air-fuel ratio variation between the cylinders is equal to or more than a predetermined level by comparing the value calculated by the value calculating unit with a predetermined value, and a second inhibiting unit which inhibits an operation of the inhibiting unit in the case that the variation level detecting unit does not detect that the degree of the air-fuel ratio variation between the cylinders is equal to or more than the predetermined level.

According to the present invention having the configuration mentioned above, in the case that the intake air amount exceeds the predetermined amount, the detection of the nick abnormality in the detecting element of the downstream side sensor by the sensor nick abnormality detecting unit is inhibited by the inhibiting unit. Therefore, in the case that the nick abnormality is not in the detecting element of the downstream side sensor or is only at an insignificant level, even if the distribution of the output of the downstream side sensor is biased to the area in which the air-fuel ratio is leaner than the theoretic air-fuel ratio according to the great air-fuel ratio variation between the cylinders, it is possible to prevent or suppress an erroneous detection that the nick abnormality exists in the detecting element of the downstream side sensor, by the sensor nick abnormality detecting unit, on the basis of the bias.

Further features of the present invention will become apparent from the following description of exemplary embodiments (with reference to the attached drawings).

DESCRIPTION OF THE EMBODIMENTS

A description will be given below of embodiments according to the present invention with reference to the accompanying drawings. First, a description will be given of a first embodiment.

Figure 1:
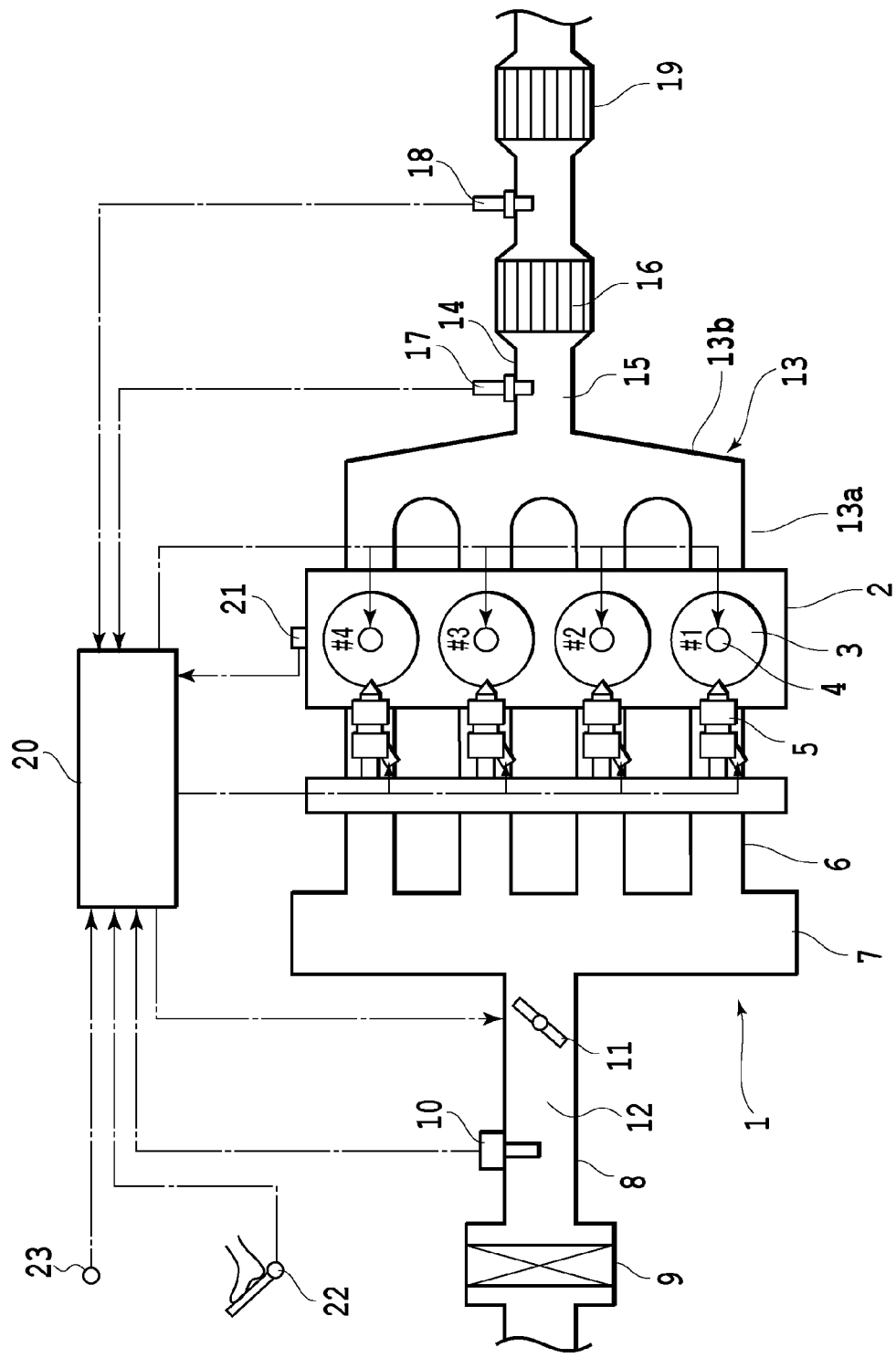
FIG. 1 is a schematic view of an internal combustion engine according to a first embodiment of the present invention.

FIG. 1 is a schematic view of an internal combustion engine according to the present first embodiment. An internal combustion engine (hereinafter, refer to as engine) 1 generates power by burning an air-fuel mixture constituted by fuel and air in an inner portion of a combustion chamber 3 formed in an engine main body 2 including a cylinder block, and reciprocating a piston in the cylinder. The engine 1 according to the present embodiment is a multi-cylinder internal combustion engine for an automobile, and more specifically an in-line four-cylinder spark igniting type internal combustion engine, that is, a gasoline engine. However, the internal combustion engine to which the present invention is applicable is not limited to the engine described above, and the number of cylinders, the type and the like are not particularly limited as long as the internal combustion engine has a plurality of cylinders. The engine 1 is mounted to a vehicle although an illustration is omitted.

Although an illustration is omitted, an intake valve and an exhaust valve are arranged every cylinder in a cylinder head of the engine 1, the intake valve opening and closing an intake port and the exhaust valve opening and closing an exhaust port. Each of the intake valves and each of the exhaust valves are opened and closed by a cam shaft. A spark plug 4 for igniting the air-fuel mixture within the combustion chamber 3 is attached every cylinder to a top portion of the cylinder head. Further, an injector (a fuel injection valve) 5 directly injecting the fuel into the combustion chamber 3 is arranged every cylinder in the cylinder head.

The intake port in each of the cylinders is connected to a surge tank 7 which is an intake air collecting chamber, via a branch pipe 6 in each of the cylinders. An intake pipe 8 is connected to an upstream side of the surge tank 7, and an air cleaner 9 is provided in an upstream end of the intake pipe 8. Further, an air flow meter 10 and an electronically controlled throttle valve 11 are assembled in the intake pipe 8 in this order from an upstream side, the air flow meter 10 serving as an intake air amount detecting unit configured to detect an intake air amount. Each of the intake port, the branch pipe 6, the surge tank 7 and the intake pipe 8 forms a part of an intake passage 12.

On the other hand, an exhaust port in each of the cylinders is connected to an exhaust manifold 13. The exhaust manifold 13 is constructed by a branch pipe 13a provided in each of the cylinders and forming an upstream portion, and an exhaust gas collecting portion 13b forming a downstream portion. An exhaust pipe 14 is connected to a downstream side of the exhaust gas collecting portion 13b. Each of the exhaust port, the exhaust manifold 13 and the exhaust pipe 14 forms a part of an exhaust passage 15. An exhaust gas purifying catalyst, which is a so-called three way catalyst, that is, a catalyst purifying device 16 is installed to the exhaust pipe 14.

Sensors generating an output corresponding to an oxygen concentration in the exhaust gas, more particularly, air-fuel ratio sensors 17 and 18 for detecting the air-fuel ratio are installed on an upstream side and a downstream side of the catalyst 16, respectively. The sensor (the upstream side sensor) 17 on the upstream side of the catalyst 16 is called here a catalyst front sensor 17, and the sensor (the downstream side sensor) 18 on the downstream side of the catalyst 16 is called here the catalyst rear sensor 18. The catalyst front sensor 17 and the catalyst rear sensor 18 are installed in the exhaust passage at positions just before and just after the catalyst 16, respectively, and each generates outputs based on the oxygen concentration in the exhaust gas.

In the present first embodiment, a catalyst including the same three way catalyst as the catalyst 16, that is, a catalyst purifying device 19 is installed also to a downstream side of the catalyst rear sensor 18.

The spark plug 4, the injector 5, the throttle valve 11 and the like mentioned above are electrically connected to an electric control unit (ECU) 20 which is constructed as a controller, that is, a control portion. The ECU 20 includes a CPU, an input and output port, a memory device which includes a ROM and a RAM, and the like, which are not shown. Further, to the ECU 20, there are electrically connected a crank angle sensor 21 for detecting a crank angle of the engine 1, an accelerator opening sensor 22 for detecting an accelerator opening degree, a vehicle speed sensor 23 for detecting a speed of a vehicle mounting the engine 1 thereon, that is, a vehicle speed, and the other various sensors, in addition to the air flow meter 10, the catalyst front sensor 17 and the catalyst rear sensor 18 which are mentioned above, via an A/D converter (not shown) or the like, as shown. The ECU 20 controls the spark plug 4, the injector 5, the throttle valve 11 and the like so that a desired engine output can be obtained on the basis of the outputs of the various sensors, thereby controlling an ignition timing, a fuel injection amount, a fuel injection timing, a throttle opening degree and the like. The throttle opening degree is controlled to an opening degree corresponding to the accelerator opening degree, and the greater the accelerator opening degree is, the greater the throttle opening degree is.

As mentioned above, the ECU 20 takes charge of respective functions of a fuel injection control unit, an ignition control unit, an intake air amount control unit and the like. Further, as is apparent from the following description, the ECU 20 takes charge of respective functions of an air-fuel ratio control unit, a sensor nick abnormality detecting unit aiming at the catalyst rear sensor 18, an inhibiting unit, a value calculating unit and a variation abnormality detecting unit.

Further, the ECU 20 detects an amount of intake air per unit time, that is, an intake air amount on the basis of the output signal from the air flow meter 10. The ECU 20 detects the number of revolutions in the engine 1 as well as detecting a crank angle itself, on the basis of a crank pulse signal from the crank angle sensor 21. Here, the "number of revolutions" means the number of revolutions per unit time, and has the same meaning as a rotating speed. Further, the ECU 20 generally sets a fuel injection amount (or a fuel injection time) by using data or the like which is previously stored in the memory device, on the basis of the intake air amount and the engine rotating speed, that is, an engine operating state. Further, the fuel injection from the injector 5 is controlled on the basis of the fuel injection amount.

Figure 2:
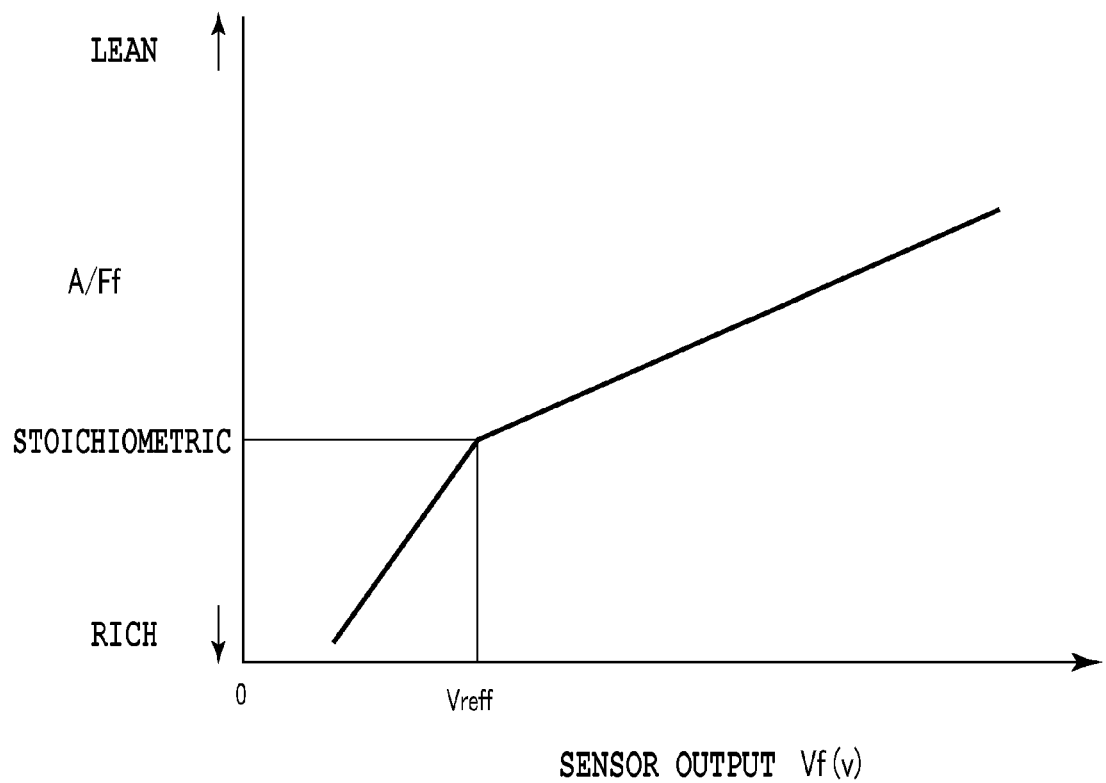
FIG. 2 is a graph showing an output characteristic of a catalyst front sensor.

By the way, the catalyst front sensor 17 is a so-called wide area air-fuel ratio sensor, and can continuously detect the air-fuel ratio over a comparatively wide range. FIG. 2 shows an output characteristic of the catalyst front sensor 17. As illustrated, the catalyst front sensor 17 outputs a voltage signal Vf having a magnitude in proportion to an air-fuel ratio (a catalyst front air-fuel ratio A/Ff). The output voltage in the case that the air-fuel ratio is stoichiometric (a theoretical air-fuel ratio, for example, A/F=14.6) is Vreff (for example, about 3.3 V).

Figure 3:
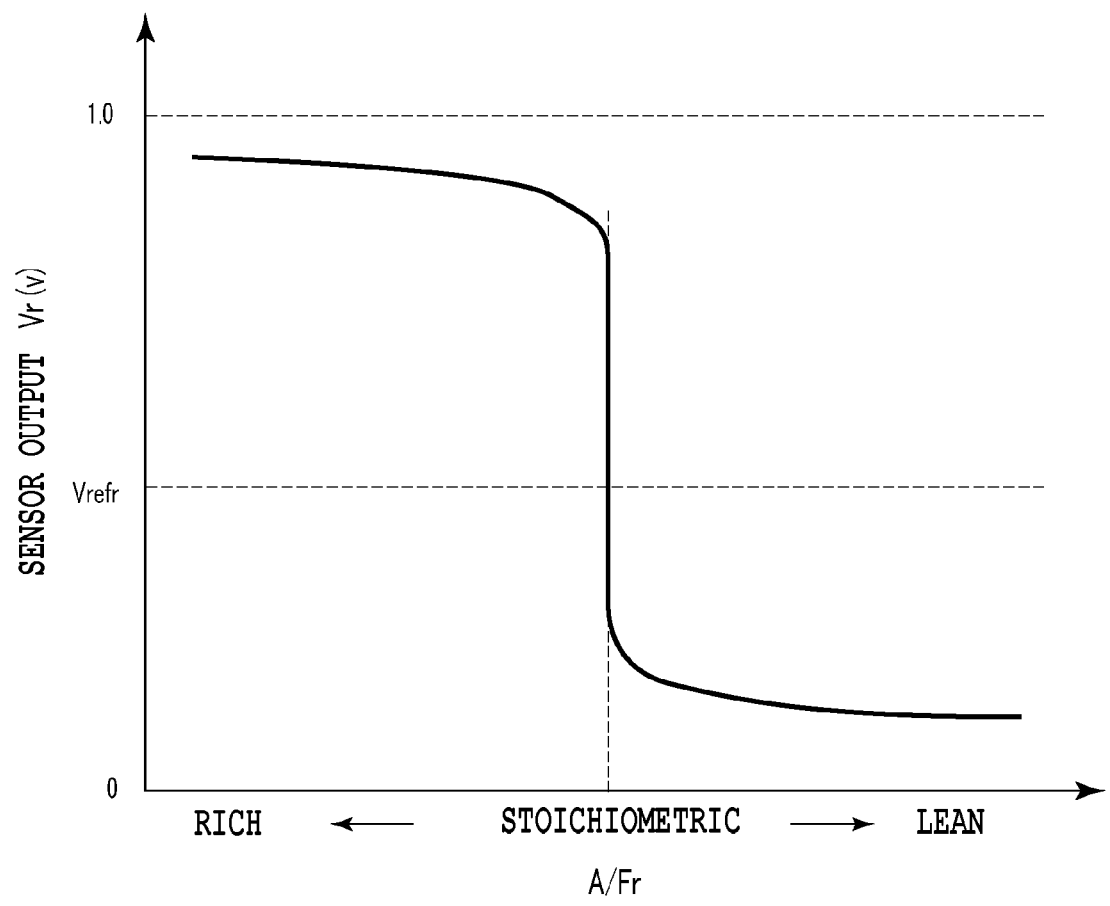
FIG. 3 is a graph showing an output characteristic of a catalyst rear sensor.

On the other hand, the catalyst rear sensor 18 is a so-called oxygen ($O_2$) sensor, and has a characteristic that an output value rapidly changes beyond the stoichiometric ratio. FIG. 3 shows an output characteristic of the catalyst rear sensor 18. As shown, an output voltage in the case that an air-fuel ratio (a catalyst rear air-fuel ratio A/Fr) is stoichiometric, that is, a stoichiometric equivalent value is Vrefr (for example, 0.45 V). The output voltage of the catalyst rear sensor 18 changes within a predetermined range (for example, 0 to 1 V). Generally, the output voltage Vr of the catalyst rear sensor 18 becomes lower than the stoichiometric equivalent value Vrefr in the case that the air-fuel ratio is leaner than the stoichiometric ratio, and the output voltage Vr of the catalyst rear sensor 18 becomes higher than the stoichiometric equivalent value Vrefr in the case that the air-fuel ratio is richer than the stoichiometric ratio.

The catalyst purifying devices 16 and 19 each include a three way catalyst, and simultaneously purify NOx, HC and CO which are the harmful components in the exhaust gas in the case that the air-fuel ratios A/F of the exhaust gas flowing into the catalyst purifying devices 16 and 19 are near the stoichiometric ratio. A width (a window) of the air-fuel ratio which can simultaneously purify these three components with a high efficiency is comparatively narrow.

The air-fuel ratio control (the stoichiometric control) for controlling the air-fuel ratio of the exhaust gas flowing into the catalyst purifying device 16 on the upstream side to the vicinity of the stoichiometric ratio is carried out by the ECU 20, during the normal operating time of the engine 1. The air-fuel ratio control includes a main air-fuel ratio control (a main air-fuel ratio feedback control) which feedback controls the air-fuel ratio (specifically the fuel injection amount) of the air-fuel mixture so that the air-fuel ratio of the exhaust gas detected by the catalyst front sensor 17 becomes a stoichiometric ratio as a predetermined target air-fuel ratio, and an auxiliary air-fuel ratio control (an auxiliary air-fuel ratio feedback control) which feedback controls the air-fuel ratio (specifically the fuel injection amount) of the air-fuel mixture so that the air-fuel ratio of the exhaust gas detected by the catalyst rear sensor 18 becomes the stoichiometric ratio. Specifically, in the main air-fuel ratio feedback control, the control is carried out so as to compute a first correction coefficient and adjust the fuel injection amount from the injector 5 on the basis of the first correction coefficient, for making the current air-fuel ratio detected on the basis of the output of the catalyst front sensor 17 follow a predetermined target air-fuel ratio. Further, further in the auxiliary air-fuel ratio feedback control, the control is carried out so as to compute a second correction coefficient on the basis of the output of the catalyst rear sensor 18, and correct the first correction coefficient obtained by the main air-fuel ratio feedback control. In the present embodiment, the predetermined target air-fuel ratio, that is, a reference value (a target value) of the air-fuel ratio is the stoichiometric ratio, and the fuel injection amount (which is called a stoichiometric equivalent amount) equivalent to the stoichiometric ratio is the reference value (the target value) of the fuel injection amount. The reference values of the air-fuel ratio and the fuel injection amount can be set to the other values. In the air-fuel ratio control, the same control amount is uniformly employed with respect to each of the cylinders.

The engine 1 includes a device diagnosing or detecting the presence of nick abnormality of the oxygen sensor as mentioned above, that is, a sensor nick abnormality detecting device (a sensor nick abnormality detecting unit) (refer, for example, to Japanese Patent Laid-Open No. 2003-14683). This is because the air-fuel ratio control cannot be appropriately carried out in this condition in the case that a nick is generated in the catalyst rear sensor 18 which is the oxygen sensor. A description will be given below of the nick abnormality of the detecting element in the catalyst rear sensor 18 which is the oxygen sensor, and a detecting process thereof. As is apparent from the following description, the ECU 20 substantially takes charge of the sensor nick abnormality detecting unit or its function.

Figure 4A:
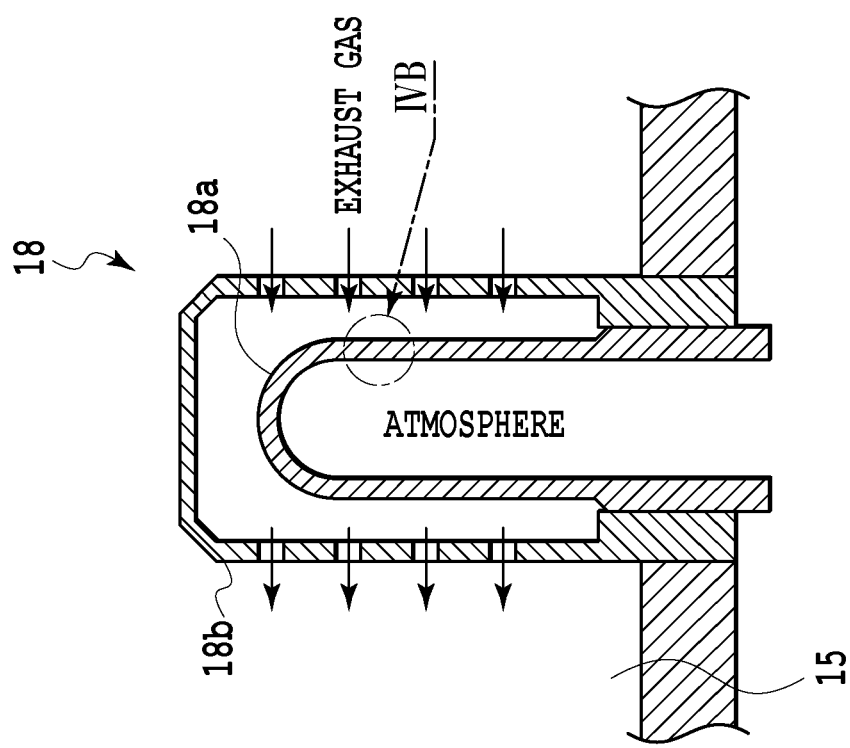
FIG. 4A is a schematic view showing a conceptual structure of an oxygen sensor which is the catalyst rear sensor.
Figure 4B:
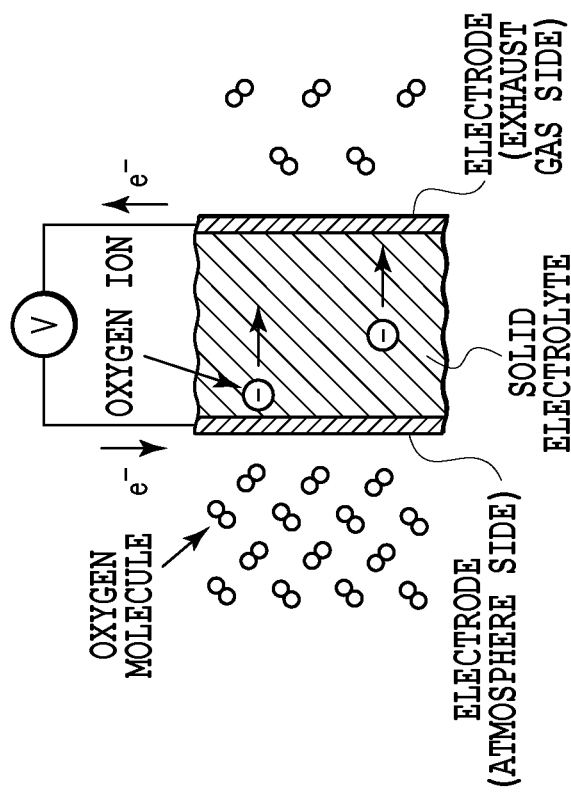
FIG. 4B is an enlarged schematic view of a portion which is surrounded by an IVB portion in the sensor in FIG. 4A.

First, a description will be given of the catalyst rear sensor 18, that is, the oxygen sensor. The catalyst rear sensor 18 is constructed as a cylinder type oxygen sensor using a solid electrolyte. The sensor 18 includes a cylinder type detecting element (sensor element) 18a which is arranged so as to protrude into the exhaust passage 15, as FIG. 4A shows its conceptual structure. The detecting element 18a exposes its inner surface to the atmosphere (the air) and exposes its outer surface to the exhaust gas which flows through a sensor cover 18b. Further, the detecting element 18a is formed by a solid electrolyte having electrodes coated on its inner and outer surfaces, as FIG. 4B shows its partial cross sectional structure. The solid electrolyte indicates a solid material in which oxygen can move in its inner portion in an ionized state, and a zirconia is utilized here. The solid electrolyte may be constructed by another material.

In the case that any difference is generated in an oxygen partial pressure, that is, an oxygen concentration between the inside atmosphere and the outside exhaust gas which are separated via the detecting element 18a mentioned above, the oxygen on the side having the higher oxygen concentration (normally, the atmosphere side) is ionized and passes through the solid electrolyte so as to move to the side having the lower oxygen concentration (normally, the exhaust gas side), for reducing the difference. The oxygen molecule accepts a tetravalent electron in an ionizing process, and discharges a tetravalent electron in a process of returning to the molecule from the ionized state. Accordingly, the electron movement is generated in the electrodes on the inner and outer surfaces of the detecting element 18a in response to the oxygen movement. As a result, the electromotive force is generated in the detecting element. The catalyst rear sensor 18 outputs the electric voltage in accordance with the difference in the oxygen partial pressure, that is, the oxygen concentration between the atmosphere and the exhaust gas as mentioned above.

On the other hand, the oxygen concentration of the exhaust gas changes in accordance with the air-fuel ratio of the burnt air-fuel mixture. For example, in the case of the air-fuel mixture burnt at the air-fuel ratio which is equal to or richer than the stoichiometric ratio, the oxygen in the air-fuel mixture is almost completely burnt. Therefore, the oxygen concentration of the exhaust gas becomes approximately zero. Further, in the case of the air-fuel ratio which is leaner than the stoichiometric ratio, the oxygen is left at the time of burning. Accordingly, the leaner the air-fuel ratio is, the higher the oxygen concentration in the exhaust gas is. On the contrary, the oxygen concentration of the atmosphere is always approximately constant. Therefore, it is possible to comprehend the air-fuel ratio of the air-fuel mixture burnt in the engine 1, on the basis of the output voltage of the sensor 18 corresponding to the oxygen concentration of the exhaust gas on the basis of the oxygen concentration of the atmosphere. This has been already described with reference to FIG. 3.

In the catalyst rear sensor 18 which is the oxygen sensor mentioned above, in the case that any nick is generated in the detecting element 18a and the inner and outer sides of the detecting element 18a are communicated, the exhaust gas in the outer portion of the detecting element intrudes into the inner portion, the difference is lost in the oxygen concentrations between the inner and outer sides, and the catalyst rear sensor 18 does not generate an electromotive force. Therefore, in the case of recognizing such an output pattern that keeps outputting a signal indicating that the oxygen concentrations in the inner and outer sides of the detecting element 18a have no difference or substantially have no difference, as a result of monitoring of the output of the catalyst rear sensor 18, it is possible to determine that a nick is generated in the detecting element 18.

Figure 5A:
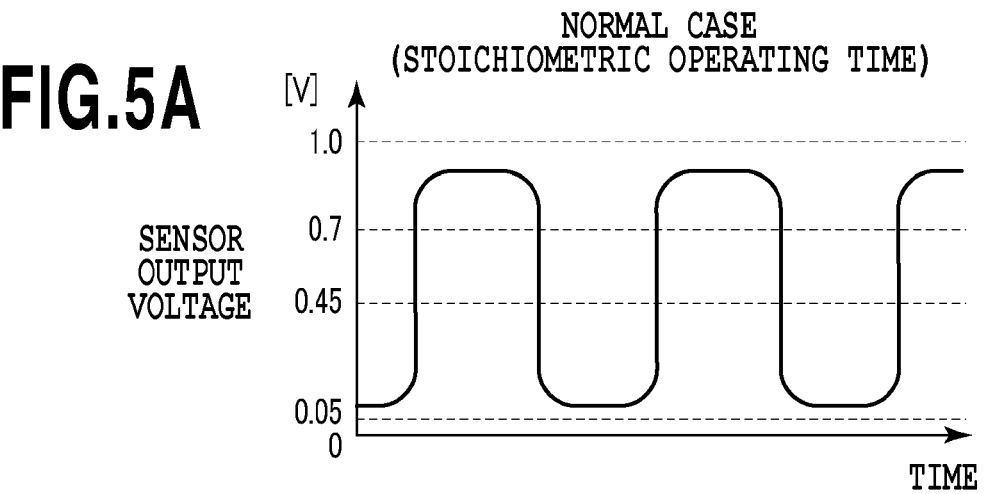
FIG. 5A is a graph showing an output wave form, by way of example, of the oxygen sensor in FIG. 4A, and is a graph showing a sensor output wave form at a stoichiometric operating time in a normal case.
Figure 5B:
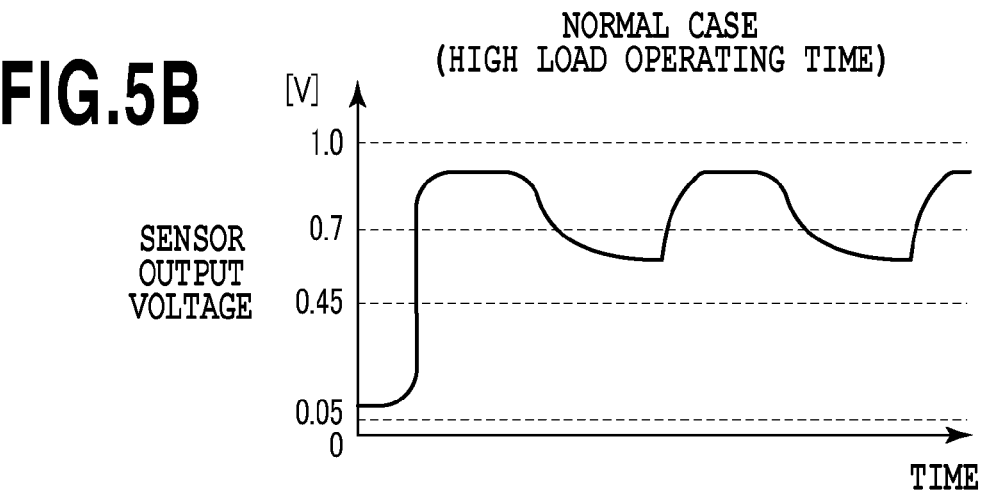
FIG. 5B is a graph showing an output wave form, by way of example, of the oxygen sensor in FIG. 4A, and is a graph showing a sensor output wave form at a high load operating time in the normal case.
Figure 5C:
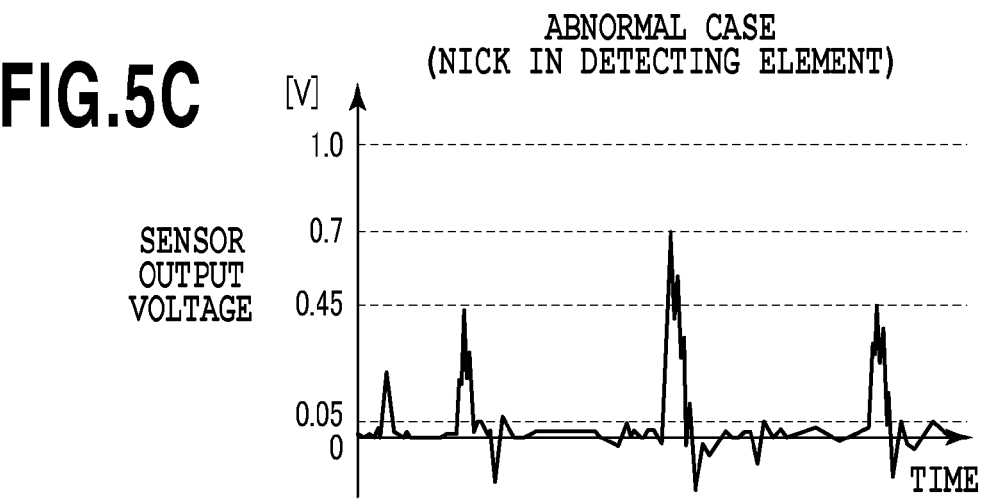
FIG. 5C is a graph showing an output wave form, by way of example, of the oxygen sensor in FIG. 4A, and is a graph showing a sensor output wave form in the case that a nick is generated in a detecting element.

Here, FIGS. 5A to 5C conceptually show examples of the output pattern of the catalyst rear sensor 18 under the engine operation. FIG. 5A shows an example of a normal output pattern of the catalyst rear sensor 18 in the case that the air-fuel ratio feedback stoichiometric control is carried out, and the stoichiometric combustion is carried out in the engine. As mentioned above, at the time of stoichiometric combustion, the output of the catalyst rear sensor 18 in the normal case shows such an output pattern that alternately repeats a higher electric voltage indicating that the air-fuel ratio is richer than the stoichiometric ratio, and a lower electric voltage indicating that the air-fuel ratio is leaner than the stoichiometric ratio.

On the other hand, in the engine 1, the combustion is carried out at an air-fuel ratio which is richer than the stoichiometric ratio, during a high load operating time. In such a case, the output of the catalyst rear sensor 18 in the normal case shows such an output pattern that the air-fuel ratio undergoes a transition in a comparatively high electric voltage area in which the air-fuel ratio is richer than the stoichiometric ratio, as exemplified in FIG. 5B.

On the contrary, the catalyst rear sensor 18 in the case that a nick is generated in the detecting element 18a generates an output having an output pattern as exemplified in FIG. 5C. In other words, in the case that a nick is generated, the output of the catalyst rear sensor 18 is held in a state in which the catalyst rear sensor 18 keeps outputting an electric voltage near "0" V indicating that there is almost no difference in the oxygen concentrations between the exhaust gas and the atmosphere as long as the catalyst rear sensor 18 is normal. The catalyst rear sensor 18, however, can occasionally output a high electric voltage in response to a rapid change of the oxygen concentration of the exhaust gas such as after returning from the fuel cut.

Figure 6A:
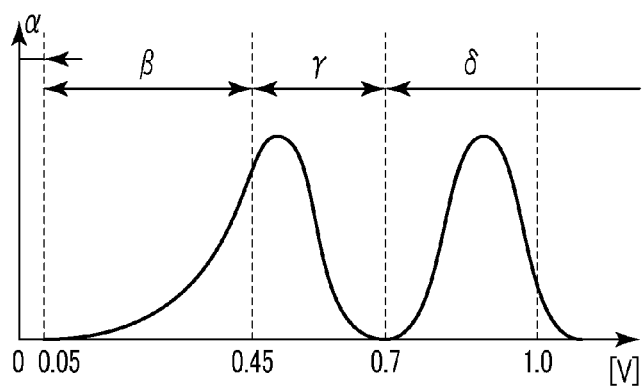
FIG. 6A is a graph showing a distribution of an output voltage of the oxygen sensor in FIG. 5A.
Figure 6B:
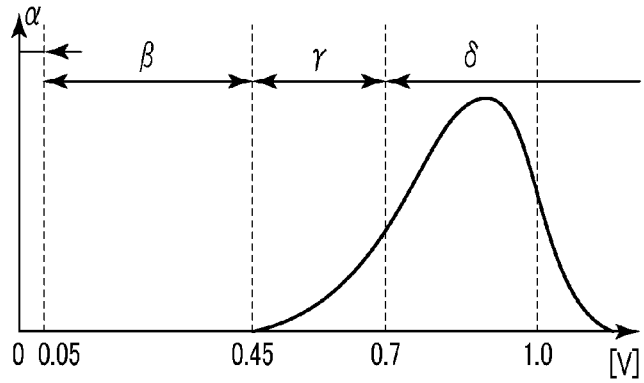
FIG. 6B is a graph showing a distribution of an output voltage of the oxygen sensor in FIG. 5B.
Figure 6C:
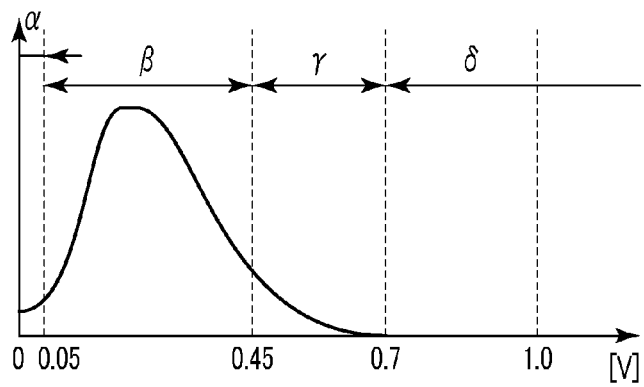
FIG. 6C is a graph showing a distribution of an output voltage of the oxygen sensor in FIG. 5C.

As mentioned above, in the case that the nick is generated in the detecting element 18a, the output pattern of the catalyst rear sensor 18 is greatly different from that in the normal case. FIGS. 6A to 6C show output distributions of the catalyst rear sensor 18 under respective conditions in FIGS. 5A to 5C. In the case that the nick is generated in the detecting element 18a, the output distribution of the catalyst rear sensor 18 is biased to a low electric voltage area in which the air-fuel ratio is leaner than the stoichiometric ratio (refer to FIG. 6C), and thus it is possible to clearly discriminate the case from the normal case (refer to FIGS. 6A and 6B). As a result, it is possible to easily and accurately determine the presence of a nick of the detecting element 18a on the basis of the output distribution of the catalyst rear sensor 18.

Figure 7:
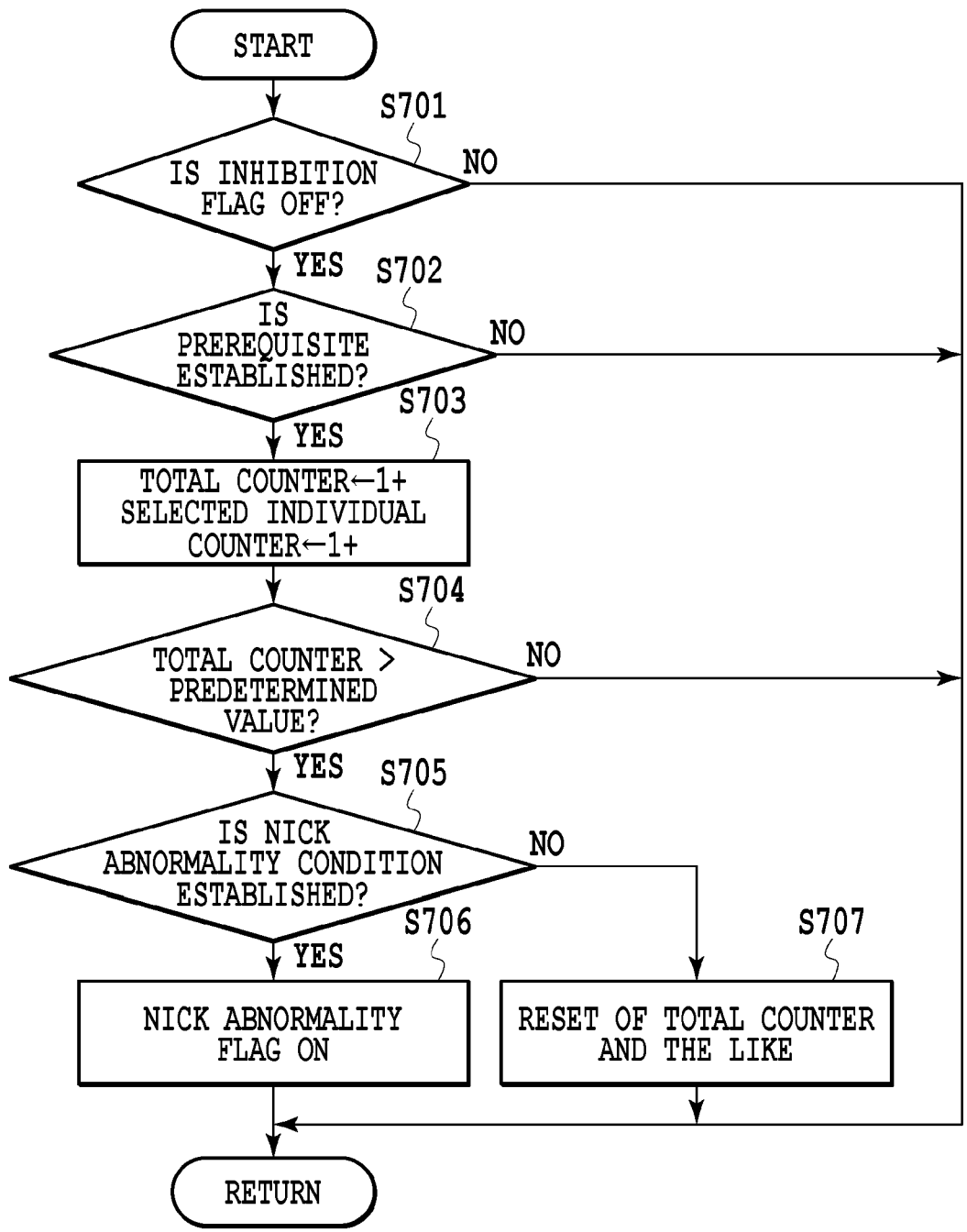
FIG. 7 is a flow chart of a process of detecting a nick abnormality in a detecting element of the catalyst rear sensor.

Accordingly, the output distribution of the catalyst rear sensor 18 is obtained from the result of monitoring the output of the catalyst rear sensor 18 during the engine operation, and a nick of the detecting element 18a is detected based on the output distribution if the nick is generated. A description will be given below of details of the process of detecting the sensor nick abnormality mentioned above, on the basis of a flowchart in FIG. 7. The process based on the flow in FIG. 7 is repeatedly carried out by the ECU 20 during the engine operation, with the catalyst rear sensor 18 as a target.

Step S701 determines whether or not an inhibition flag is OFF. The inhibition flag is OFF in an initial state. The inhibition flag will be mentioned later. If step S701 makes a negative determination, the routine is finished. Accordingly, in this case, each of steps in FIG. 7 described below is not carried out, and the detection of the nick abnormality in the detecting element 18a of the catalyst rear sensor 18 is not substantially carried out.

If step S701 makes an affirmative determination, the subsequent step S702 determines whether or not a prerequisite is established. As the prerequisite, four conditions are defined, including a condition that a vehicle speed is equal to or higher than a predetermined speed (a condition a1), a condition that the vehicle is not under an idle operation (a condition a2), a condition that the vehicle is not under a fuel cut (a condition a3), and a condition that an intake air amount is equal to or more than a predetermined air amount (a first predetermined amount) (a condition a4). Further, in the case that four conditions are all established, step S702 makes an affirmative determination, and in the case that any one of them is not established, step S702 makes a negative determination. However, the prerequisite is not limited to these conditions (from the conditional to the condition a4), but any additional condition may be added, for example. The prerequisite is preferably defined so that a certain degree of intake air amount is secured (the condition a4 is established), that is, the exhaust amount is secured, and the air-fuel ratio of the air-fuel mixture is within a predetermined air-fuel ratio area. Note that, it is preferable that the air-fuel ratio feedback stoichiometric control is carried out in the case that the prerequisite is established.

In the case that step S702 makes the affirmative determination, a total counter is increased by one in step S703. The total counter is zero in an initial state, and is increased (incremented) by one every time step S703 is reached. Further, in step S703, the output (electric voltage) of the catalyst rear sensor 18 is acquired (sampled), and is sorted into any corresponding area of four areas in FIGS. 6A to 6C, and an individual counter relating to the corresponding area is increased (incremented) by one. In other words, four individual counters are provided.

The areas in FIGS. 6A to 6C are set to a first area α, a second area β, a third area γ and a fourth area δ in this order from a lower voltage area. The first area α is an electric voltage area (0.05 V or lower) in which the catalyst rear sensor 18 hardly outputs the electric voltage, the second area β is an electric voltage area (0.05 to 0.45 V) in which the catalyst rear sensor 18 outputs generally in the case that the air-fuel ratio of the air-fuel mixture is leaner than the stoichiometric ratio when the catalyst rear sensor 18 is normal, the third area γ is an intermediate electric voltage area (0.45 to 0.7 V) between the second area β and the fourth area δ, and the fourth area δ is an electric voltage area (0.7 V or higher) in which the catalyst rear sensor 18 outputs generally in the case that the air-fuel ratio of the air-fuel mixture is richer than the stoichiometric ratio when the catalyst rear sensor 18 is normal.

The operation (counting) of the total counter, the sensor output sampling of the catalyst rear sensor 18 and the operation (counting) of the individual counters as described above are carried out as long as steps S701 and S702 make the affirmative determinations.

Further, step S704 determines whether or not the total counter exceeds a predetermined value. The predetermined value is previously set as a value which corresponds to a monitoring time for making the nick abnormality in the detecting element 18a of the catalyst rear sensor 18 detectable on the basis of experiments.

If step S704 makes a negative determination, the routine is finished. On the other hand, if step S704 makes an affirmative determination, step S705 determines whether or not a condition for determining or detecting the nick abnormality in the detecting element 18a of the catalyst rear sensor 18 is established. Here, three conditions are defined as conditions for determining the nick abnormality, and include a condition that the individual counter in the first area α is equal to or more than a first predetermined abnormal value (a condition b1), a condition that the individual counter in the fourth area δ is less than a second predetermined abnormal value (a condition b2), and a condition that the sum of the individual counter in the second area β and the individual counter in the third area γ is less than a third predetermined abnormal value (a condition b3). If these three conditions (from the condition b1 to the condition b3) are all established, step S705 makes an affirmative determination, that is, determines that a nick abnormality exists.

Further, in the case that step S705 makes an affirmative determination, the condition for detecting the nick abnormality in the detecting element 18a of the catalyst rear sensor 18 is established. Therefore, a nick abnormality flag which is OFF in an initial state is turned ON in step S706. As a result, an alarm lamp provided in a front panel of a driver seat or the like is turned on. Note that, a previously set control for the case that the nick abnormality is detected in the catalyst rear sensor 18 may be carried out, without being limited to the lighting of the alarm lamp. For example, a fuel injection control for the case that the catalyst rear sensor 18 is abnormal may be carried out by introducing a predetermined guard for the auxiliary air-fuel ratio feedback control, for example, setting the second correction coefficient to a predetermined value or a value within a predetermined range.

On the other hand, in the case that step S705 makes a negative determination, the nick abnormality in the catalyst rear sensor 18 is not detected, that is, the nick abnormality does not exist. Therefore, the total counter and four individual counters are reset in step S707. As a result, the detection of the nick abnormality in the catalyst rear sensor will be repeatedly carried out. Note that, the nick abnormality flag may be further set to OFF in step S707.

Note that, here, establishment of all the conditions from (condition b1) to (condition b3) is required for detecting or determining the nick abnormality in the detecting element 18a of the catalyst rear sensor 18 as mentioned above. However, the nick abnormality detecting condition is not limited to them. As mentioned above, in the case that the detecting element 18a has a nick, the distribution of the output of the catalyst rear sensor 18 is biased to the area in which the air-fuel ratio is leaner than the stoichiometric ratio. Various conditions which are found by paying attention to the characteristic can be defined as the nick abnormality detecting condition.

The engine 1 having the sensor nick abnormality detecting unit with such a catalyst rear sensor 18 as a target further includes a device for detecting an air-fuel ratio variation abnormality between the cylinders, that is a value calculating unit which calculates a value indicating a degree of the air-fuel ratio variation between the cylinders, and a variation abnormality detecting unit which detects the presence of air-fuel ratio variation abnormality between the cylinders. A description will be given below of the air-fuel ratio variation between the cylinders and the detecting process thereof. Note that, as is apparent from the following description, the ECU 20 substantially takes charge of the value calculating unit and the variation abnormality detecting unit or their functions.

First, a description will be given of the air-fuel ratio variation between the cylinders and a calculation of values indicating its degree. For example, in a partial cylinder (particularly one cylinder) of all the cylinders, malfunction of the injector 5 may be generated, and variation (imbalance) in an air-fuel ratio may be generated between the cylinders. For example, it is the case that the fuel injection amount of the #1 cylinder is more than the fuel injection amount of each of the other #2, #3 and #4 cylinders due to a defective valve close of the injector 5, and the air-fuel ratio of the #1 cylinder is greatly deviated to the rich side from the air-fuel ratio of each of the other #2, #3 and #4 cylinders.

Even in this case, there is a case that the air-fuel ratio of the total gas (the exhaust gas after being merged) supplied to the catalyst front sensor 17 can be stoichiometrically controlled by applying a comparatively great correction amount on the basis of the air-fuel ratio feedback control mentioned above. However, in the light of each of the cylinders, the air-fuel ratio of the #1 cylinder is greatly richer than the stoichiometric ratio, the air-fuel ratios of the #2, #3 and #4 cylinders are leaner than the stoichiometric ratio, and the air-fuel ratio as a whole balance is just stoichiometric. Therefore, this case is apparently undesirable on emission.

Further, the fuel supplied to the combustion chamber is a chemical compound including carbon and hydrogen. Therefore, in the case that the air-fuel ratio of the air-fuel mixture supplied to the combustion is an air-fuel ratio which is closer to the rich side than the stoichiometric ratio, an unburnt substance such as HC, CO and $H_2$ is generated as an intermediate product, and the closer to the rich side the air-fuel ratio is, the more the unburnt substance is combined with the oxygen, that is, the more rapidly the oxidation combustion probability is reduced. As a result, the closer to the rich side the air-fuel ratio is, the more the amount of the unburnt substance discharged from the combustion chamber is increased. This is applied in the same manner to the case that the degree of the air-fuel ratio variation between the cylinders is enlarged, and is shown in FIG. 8.

Figure 8:
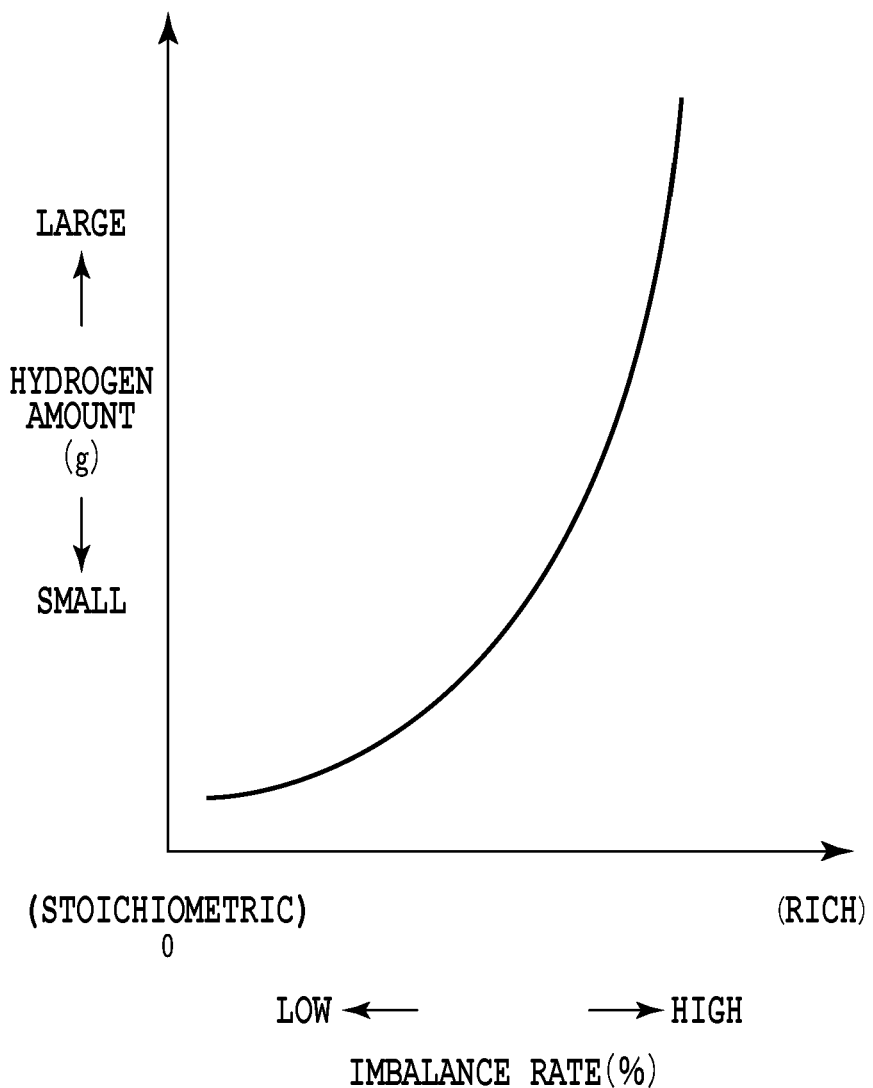
FIG. 8 is a graph showing a relationship between an imbalance rate and a hydrogen amount discharged to the exhaust passage.

FIG. 8 is a graph showing a change of a hydrogen discharging amount with respect to the air-fuel ratio in the rich side or an imbalance rate. The imbalance rate (%) is a parameter indicating the variation degree, that is, the imbalance degree of the air-fuel ratio between the cylinders. In other words, the imbalance rate is a value indicating what rate the fuel injection amount of the cylinder (an imbalance cylinder) which generates a fuel injection amount deviation is deviated from the fuel injection amount of the cylinders (balance cylinders) which do not generate the fuel injection amount deviation, in the case that only one cylinder generates the fuel injection amount deviation of all the cylinders. The imbalance rate is expressed by a formula $IB=(Qib-Qs)/Qs \times 100$ in which IB is the imbalance rate, Qib is the fuel injection amount of the imbalance cylinder, and Qs is the fuel injection amount of the balance cylinder, that is, a reference fuel injection amount. The greater the imbalance rate IB or its absolute value is, the greater the fuel injection amount deviation of the imbalance cylinder is with respect to the balance cylinders, and the greater the degree of the air-fuel ratio variation between the cylinders is. Therefore, it is known from FIG. 8 that the hydrogen discharging amount increases as the degree of the air-fuel ratio variation between the cylinders increases.

On the other hand, the catalyst front sensor 17 which is the so-called wide area air-fuel ratio sensor generally includes a diffusion resistance layer, and generates an output in accordance with an amount of oxygen (an oxygen concentration or an oxygen partial pressure) which has reached an exhaust gas side electrode layer (a detecting element surface) of the catalyst front sensor 17 while passing through the diffusion resistance layer. However, the output of the catalyst front sensor 17 also depends on an amount (a concentration or a partial pressure) of the unburnt substance passing through the diffusion resistance layer.

The hydrogen is a molecule which is smaller than HC and CO. Accordingly, the hydrogen tends to diffuse the diffusion resistance layer of the catalyst front sensor 17 in comparison with the other unburnt substances. In other words, a hydrogen priority diffusion is generated in the diffusion resistance layer.

In the case that the degree of the air-fuel ratio variation between the cylinders becomes large, the output of the catalyst front sensor 17 becomes the one corresponding to the air-fuel ratio which is closer to the rich side than the true air-fuel ratio, due to the hydrogen priority diffusion. Therefore, since the air-fuel ratio closer to the rich side than the true air-fuel ratio is detected by the catalyst front sensor 17, the greater correction to the lean side is carried out on the basis of the air-fuel ratio feedback control mentioned above, in comparison with the case that the air-fuel ratio variation between the cylinders does not exist or hardly exists. Therefore, for example, the catalyst rear sensor 18 which is the oxygen sensor more strongly tends to generate the output biased to the lean side.

This tendency is applied in the same manner to the case that the fuel injection amount of the imbalance cylinder is smaller than that of the balance cylinder, as well as the case that the fuel injection amount of the imbalance cylinder is larger than that of the balance cylinder. In the case that the fuel injection amount of the imbalance cylinder is smaller than that of the balance cylinder, the fuel injection amount of the other balance cylinder(s) is increased on the basis of the air-fuel ratio feedback control, so as to compensate a shortfall of the fuel injection amount of the imbalance cylinder. Therefore, a lot of hydrogen is discharged from the balance cylinders in comparison with the case that the air-fuel ratio variation between the cylinders does not exist or hardly exists. The tendency that the catalyst front sensor 17 generates the output corresponding to the air-fuel ratio closer to the rich side than the true air-fuel ratio is enhanced due to the hydrogen. Therefore, even in the case that the fuel injection amount of the imbalance cylinder is smaller than that of the balance cylinder, the air-fuel ratio feedback control is carried out in the same manner. As a result, the catalyst rear sensor 18 which is the oxygen sensor more strongly tends to generate the output biased to the lean side.

As mentioned above, it is apparent that the air-fuel ratio variation between the cylinders causing such the phenomenon is not preferable on the control of the air-fuel ratio. Therefore, it is preferable that the air-fuel ratio variation to a certain degree or more is detected as an abnormality. Accordingly, a value indicating a degree of the air-fuel ratio variation between the cylinders is calculated as mentioned below, and the air-fuel ratio variation abnormality between the cylinders is detected on the basis of the value.

In the present embodiment, the value indicating the degree of the air-fuel ratio variation between the cylinders is calculated on the basis of the output of the catalyst front sensor 17 which is the air-fuel ratio sensor, and the variation abnormality is detected on the basis of the value.

Figure 9:
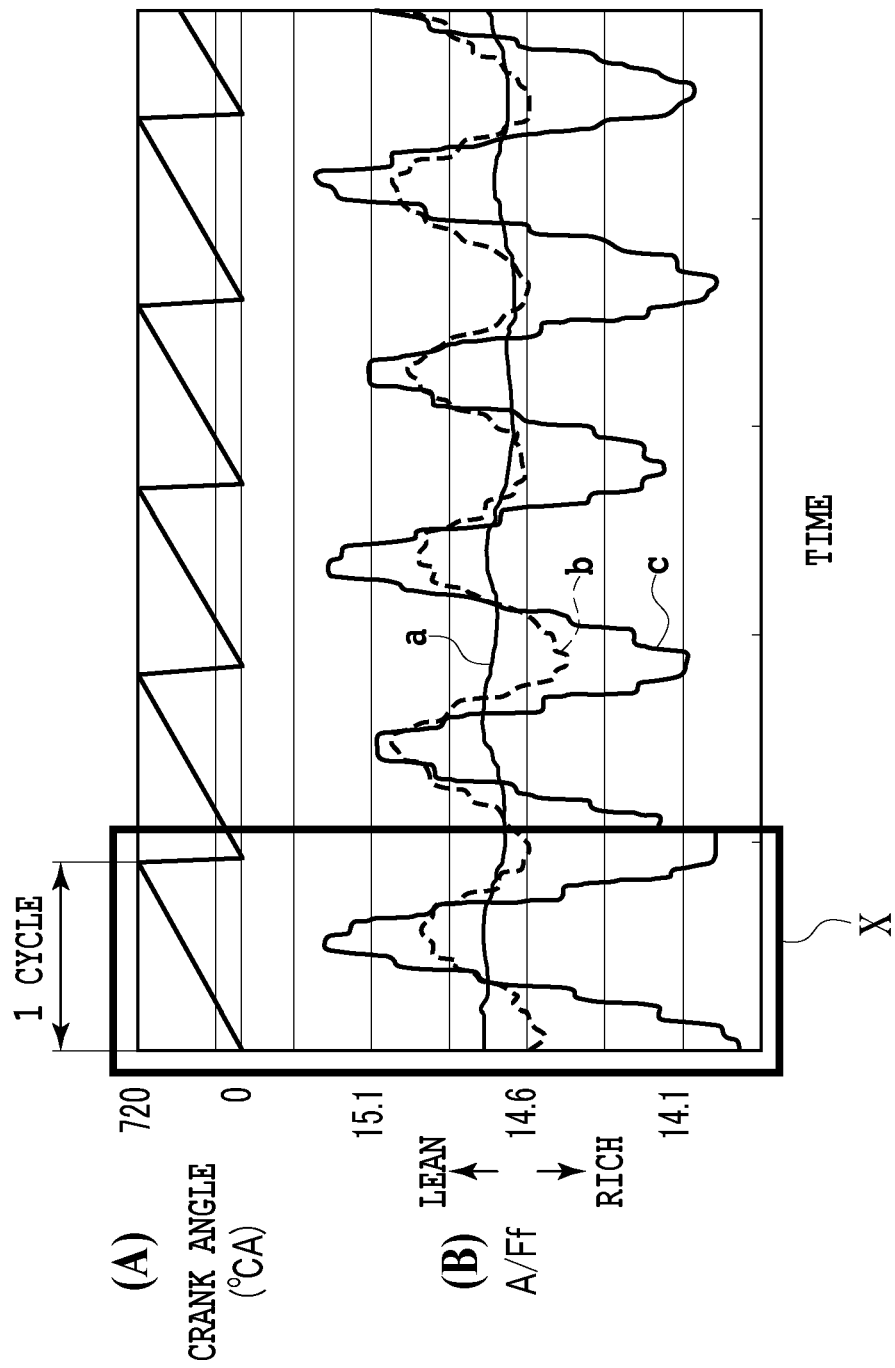
FIG. 9 is a graph showing a fluctuation, by way of example, of an exhaust gas air-fuel ratio corresponding to a degree of an air-fuel ratio variation between cylinders.

As shown in FIG. 9, in the case that the air-fuel ratio variation is generated between the cylinders, the fluctuation of the exhaust gas air-fuel ratio becomes greater during 1 engine cycle (=720° C.A). Air-fuel ratio lines a, b and c in FIG. 9 (B) respectively show examples of an air-fuel ratio A/Ff detected by the catalyst front sensor 17, in the case that the air-fuel ratio variation between the cylinders does not exist, the case that only one cylinder forms the rich deviation with 20% imbalance rate, and the case that only one cylinder forms the rich deviation with 50% imbalance rate. As shown in FIG. 9, the greater a degree or a level of the air-fuel ratio variation between the cylinders, that is, the imbalance is, the greater an amplitude of the air-fuel ratio fluctuation is. This is applied in the same manner to the case of the lean deviation.

As mentioned above, the greater the imbalance rate is, that is, the greater the degree of the air-fuel ratio variation between the cylinders is, the greater the output fluctuation of the catalyst front sensor 17 is. Therefore, in the present embodiment, an output fluctuation parameter X expressing the output fluctuation degree of the catalyst front sensor 17 is calculated by utilizing this characteristic, and is used as a value indicating the degree or the level of the air-fuel ratio variation between the cylinders.

Figure 10:
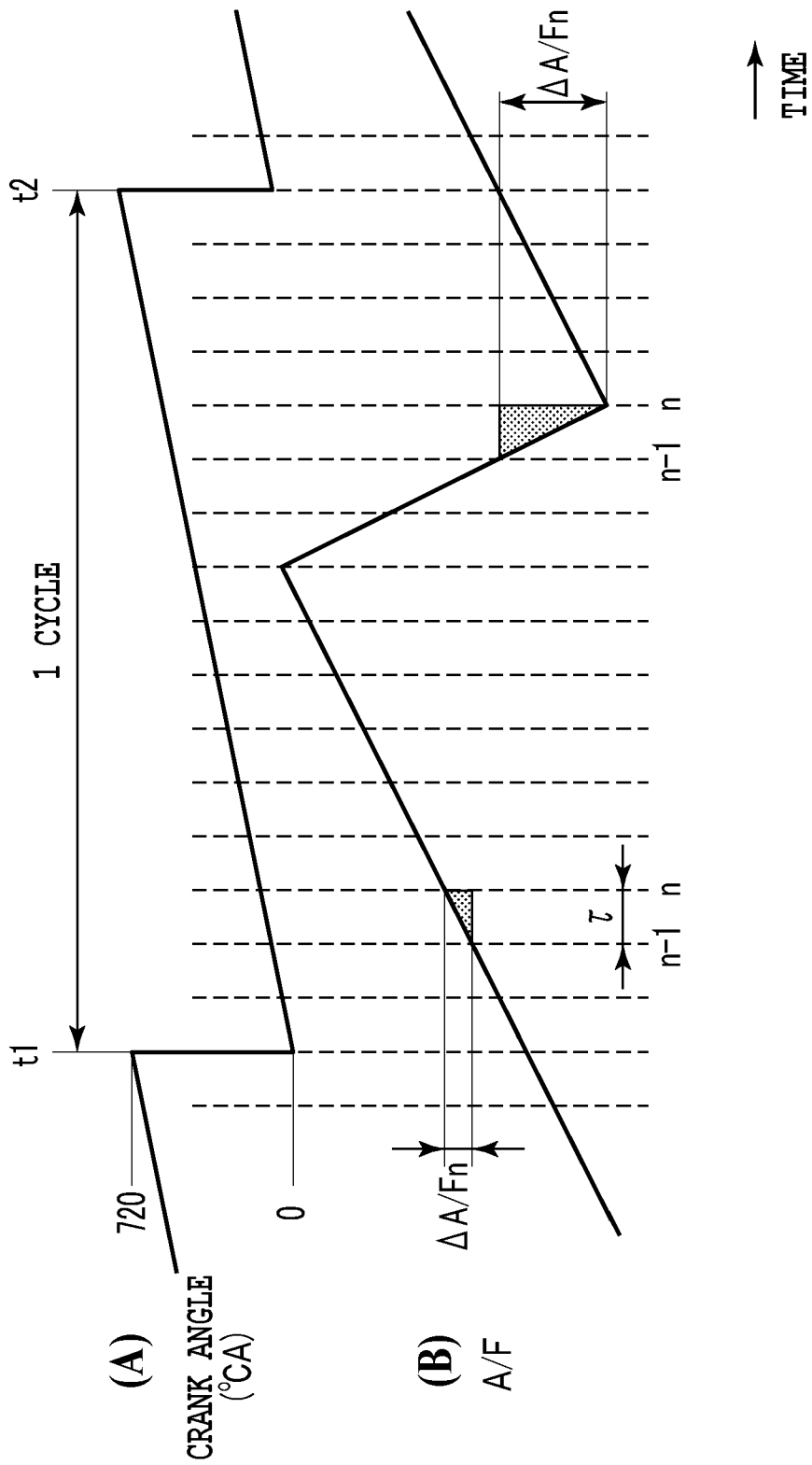
FIG. 10 is an enlarged schematic view corresponding to a portion X in FIG. 9.

A description will be given below of a method of calculating the output fluctuation parameter X. FIG. 10 is an enlarged schematic view which corresponds to the portion X in FIG. 9, and particularly shows the fluctuation of the output of the catalyst front sensor 17 within 1 engine cycle in a simplified manner. The output of the catalyst front sensor employs a value obtained by converting an output voltage Vf of the catalyst front sensor 17 into the air-fuel ratio A/Ff. However, the output voltage Vf of the catalyst front sensor 17 can be also directly used.

As shown in FIG. 10 (B), the ECU 20 acquires a value of the catalyst front sensor output A/F every predetermined sampling period $\tau$ (unit time, for example, 4 ms) within 1 engine cycle. Further, the ECU 20 obtains a difference $\Delta A/Fn$ (=A/Fn−A/Fn−1) between a value A/Fn which is acquired at this timing (a second timing), and a value A/Fn−1 which is acquired at the preceding timing (a first timing). The difference $\Delta A/Fn$ can be reworded as a differential value or an inclination at this timing.

Most simply, the difference $\Delta A/Fn$ or a magnitude (an absolute value) thereof expresses the fluctuation of the output of the catalyst front sensor 17. This is because the greater the fluctuation degree is, the greater the inclination of the air-fuel ratio line is, and the greater the absolute value of the difference $\Delta A/Fn$ is. Accordingly, the difference $\Delta A/Fn$ in a predetermined 1 timing or its magnitude can be set to the output fluctuation parameter.

In the present embodiment, however, the difference $\Delta A/F$ is converted to its magnitude, that is, the absolute value thereof, in the following description. Further, in order to improve a precision, an average value of a plurality of differences $\Delta A/Fn$ is set to the output fluctuation parameter. Particularly, in the present embodiment, the outputs of the catalyst front sensor 17 may be acquired within 1 engine cycle, or preferably during the engine cycles more than 1 engine cycle, the differences $\Delta A/Fn$ at the respective timings are calculated, the absolute values of the differences $\Delta A/F$ are integrated, the final integrated value is divided by the sampling number, and the average value of the absolute values of the differences $\Delta A/Fn$ within a predetermined engine cycle is obtained. The final average value thus obtained is set to the output fluctuation parameter X. The output fluctuation parameter X becomes greater as the fluctuation degree of the catalyst front sensor output becomes greater.

Figure 11:
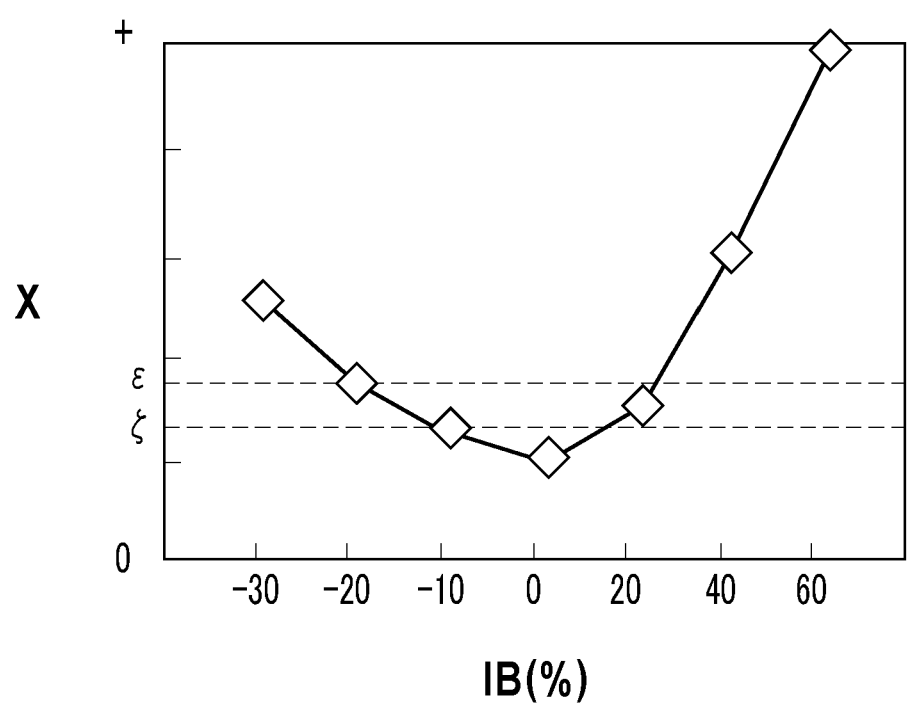
FIG. 11 is a graph showing a relationship between an imbalance rate and an output fluctuation parameter.

FIG. 11 shows a relationship between the imbalance rate IB (%) and the output fluctuation parameter X. As shown, a strong correlation exists between the imbalance rate IB and the output fluctuation parameter X, and the parameter X increases as the absolute value of the imbalance rate IB increases (as the degree of the air-fuel ratio variation between the cylinders becomes greater). Accordingly, it is possible to detect the generation of the air-fuel ratio variation between the cylinders, particularly the air-fuel ratio variation between the cylinders which is equal to or greater than a predetermined level (the air-fuel ratio variation abnormality between the cylinders), on the basis of the output fluctuation parameter X.

Figure 12:
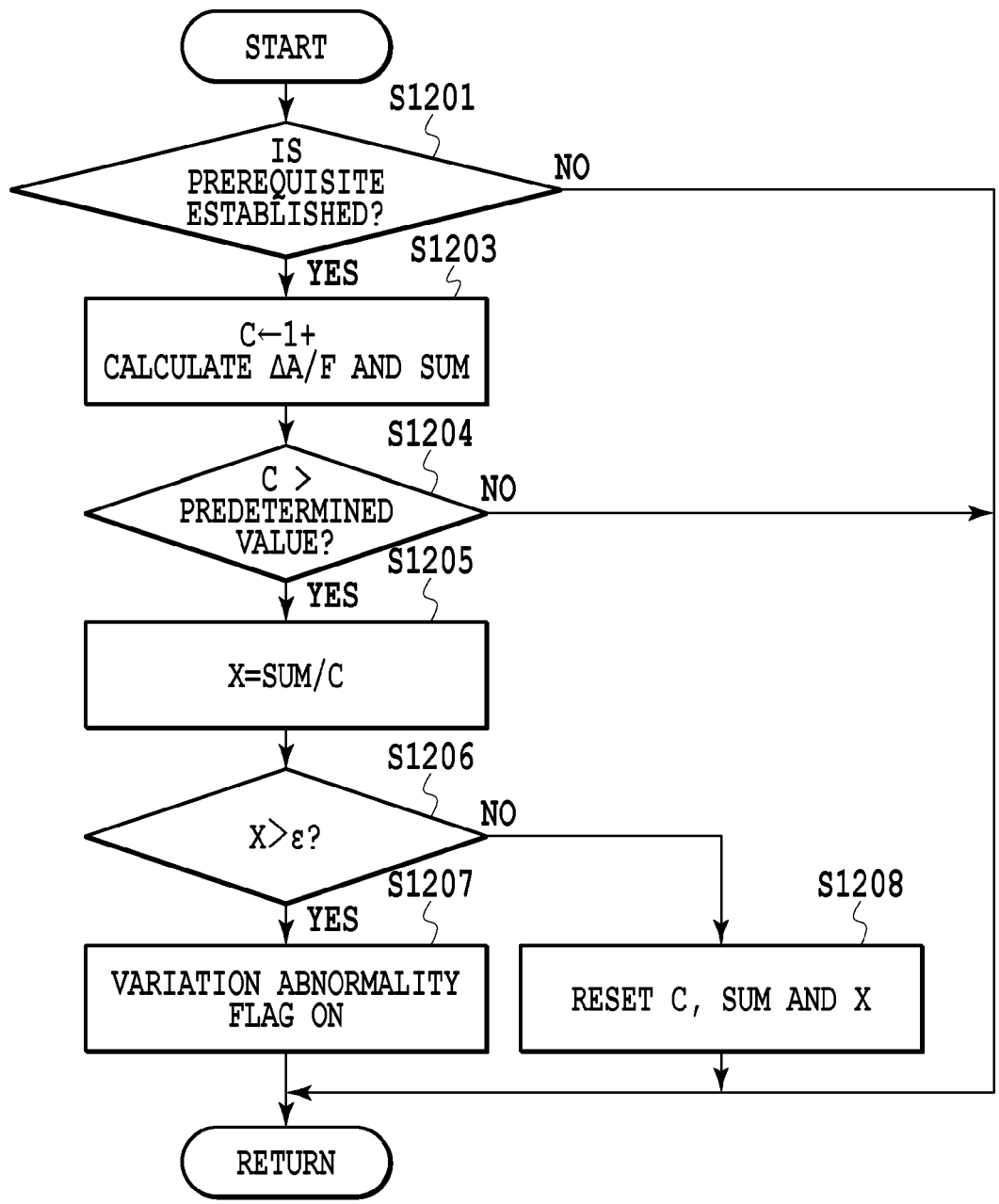
FIG. 12 is a flow chart of a process of detecting an air-fuel ratio variation abnormality between the cylinders.

A description will be given further of a process of detecting the air-fuel ratio variation abnormality between the cylinders, on the basis of a flow chart in FIG. 12. The process based on the flow in FIG. 12 is repeatedly carried out by the ECU 20 during the engine operation.

Step S1201 determines whether or not a prerequisite for detecting the air-fuel ratio variation abnormality between the cylinders is established. Here, the establishment of the prerequisite is determined in the case that the engine operating state is in a predetermined operating state. Specifically, it is determined on the basis of an engine rotating speed and an engine load (for example, an intake air amount and an accelerator opening degree) whether or not the engine operating state is in the predetermined operating state. Note that, here, the predetermined operating state is an operating state in which the air-fuel ratio control for controlling the air-fuel ratio to the vicinity of the stoichiometric ratio, that is, the stoichiometric control is carried out, as mentioned above. Various conditions, however, can be added to the prerequisite, or can be replaced by the prerequisite.

In the case that step S1201 makes an affirmative determination, step S1203 calculates the difference ΔA/F on the basis of the acquired output of the catalyst front sensor 17 as already described above, and further adds an absolute value thereof to an integrated value SUM of the previous |ΔA/F| (SUMn=SUMn−1+|ΔA/Fn|). The counter C is increased one by one (incremented) every computation in step S1203.

Further, step S1204 determines whether or not the counter C exceeds a predetermined value. The predetermined value here is a predetermined sampling number, and is previously set as a sampling number, that is, a time allowing the detection of the air-fuel ratio variation abnormality between the cylinders, on the basis of experiments. In the case that step S1204 makes a negative determination, the routine is finished. As mentioned above, until the prerequisite is established and the sampling number reaches the predetermined value, the difference of the detected air-fuel ratios is obtained on the basis of the output of the catalyst front sensor 17 and the absolute value keeps being added.

In the case that step S1204 makes an affirmative determination, the output fluctuation parameter X is calculated in step S1205. The output fluctuation parameter X is calculated by dividing the integrated value SUM which is calculated until the moment by the value of the counter C (X=SUM/C).

Further, step S1206 determines whether or not the output fluctuation parameter X calculated in step S1205 exceeds a predetermined value $\epsilon$. The predetermined value $\epsilon$ is expressed in FIG. 11, and is previously set as a threshold value for determining whether or not the degree of the air-fuel ratio variation between the cylinders is recognized to be abnormal, on the basis of experiments. The predetermined value is not limited to the value $\epsilon$ expressed in FIG. 11, but may employ another value.

Further, in the case that step S1206 makes an affirmative determination, the degree of the air-fuel ratio variation between the cylinders is great enough to be recognized as the variation abnormality. In step S1207, a variation abnormality flag which is set to OFF in an initial state is turned ON. As a result, an alarm lamp provided in a front panel of a driver seat or the like is turned on. In this case, the variation abnormality flag can be set to OFF by a service person. Note that, a previously set control for the case that the air-fuel ratio variation abnormality between the cylinders is detected may be carried out, without being limited to the lighting of the alarm lamp. For example, in the case that the air-fuel ratio variation abnormality between the cylinders is detected as mentioned above, the engine 1 can be variously operated in accordance with the degree of the air-fuel ratio variation abnormality between the cylinders, for example, on the basis of the output fluctuation parameter X calculated in step S1205.

On the other hand, in the case that step S1206 makes a negative determination, the air-fuel ratio variation abnormality between the cylinders does not exist. Accordingly, the counter C, the integrated value SUM and the output fluctuation parameter X are reset in step S1208. As a result, the detection of the air-fuel ratio variation abnormality between the cylinders will be carried out repeatedly. Further, the variation abnormality flag may be set to OFF in step S1208.

As mentioned above, the process of detecting the nick abnormality in the detecting element of the catalyst rear sensor 18 which is the oxygen sensor, and the process of detecting the air-fuel ratio variation abnormality between the cylinders are carried out in parallel. However, as mentioned above, the catalyst rear sensor 18 which is the oxygen sensor more strongly tends to generate the output biased to the lean side as the degree of the air-fuel ratio variation between the cylinders becomes greater. Further, since the fuel injection amount is generally increased particularly according to the large amount of intake air amount, the influence of the hydrogen applied to the output of the catalyst rear sensor 18 tends to be increased. Accordingly, in the case that the engine operation having the large amount of intake air amount is carried out when the degree of the air-fuel ratio variation between the cylinders is high, the catalyst rear sensor 18 further strongly tends to generate the output which is closer to the lean side than the stoichiometric ratio. As a result, there is a possibility that the nick abnormality generation is erroneously detected in the detecting element of the catalyst rear sensor 18.

Accordingly, in the present first embodiment, the detection of the nick abnormality in the detecting element of the catalyst rear sensor 18, that is, the actuation of the detecting unit is inhibited, for preventing the erroneous detection of the sensor nick abnormality in the case that the intake air amount is large as mentioned above. This inhibition is carried out by a portion serving as the inhibiting unit which the ECU 20 takes charge of.

Figure 13:
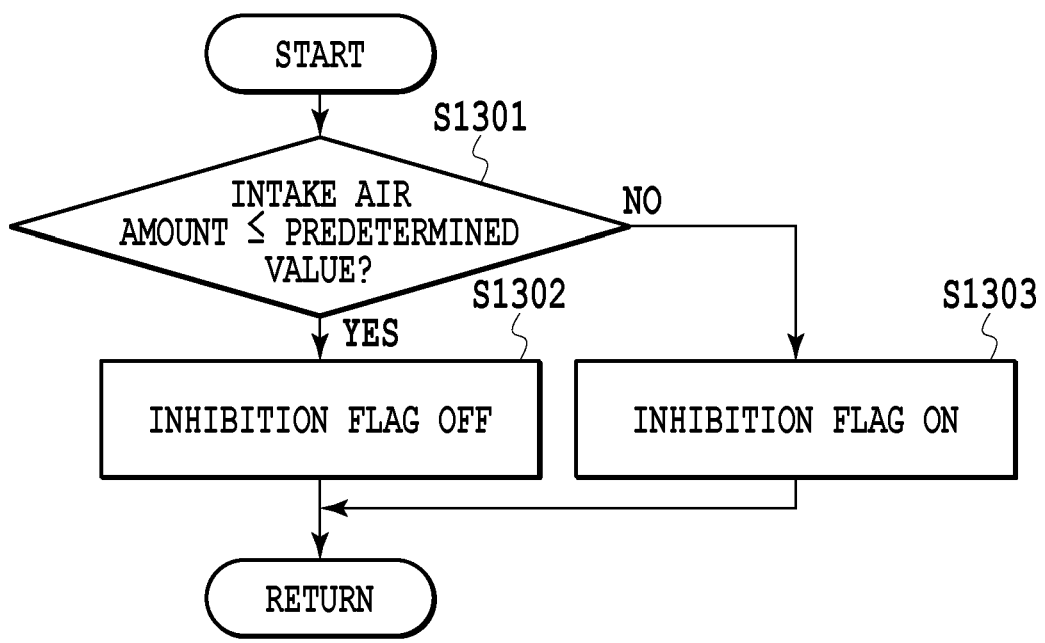
FIG. 13 is a flow chart of a process of inhibiting detection of a sensor nick abnormality in the first embodiment.

A description will be given below of an inhibiting process with respect to the process of detecting the nick abnormality in the detecting element of the catalyst rear sensor 18 on the basis of a flow chart in FIG. 13. The process based on the flow in FIG. 13 is repeatedly carried out by the ECU 20 during the engine operation.

First, step S1301 determines whether or not the intake air amount is equal to or less than a predetermined value. This determination corresponds to the determination whether or not the intake air amount exceeds a predetermined value (a second predetermined amount). The ECU 20 calculates the intake air amount on the basis of the output of the air flow meter 10. The predetermined value is previously defined on the basis of experiments, while taking into consideration the possibility that the nick abnormality generation is erroneously detected in the detecting element 18a of the catalyst rear sensor 18 on the basis of the air-fuel ratio variation, in the case that the degree of the air-fuel ratio variation between the cylinders is great, for example, there is the air-fuel ratio variation abnormality between the cylinders. The predetermined value in step S1301 is an air amount which is greater than the predetermined air amount (the first predetermined amount) of the above condition (the condition a4).

In the case that step S1301 makes an affirmative determination, an inhibition flag is set to OFF in step S1302. The inhibition flag is used for selecting whether or not to perform the process of detecting the nick abnormality in the detecting element 18a of the catalyst rear sensor 18, and relates to step S701 mentioned above. In other words, in the case that the inhibition flag is OFF, step S701 makes an affirmative determination, that is, the execution of the detecting process of the nick abnormality in the detecting element of the catalyst rear sensor 18 described on the basis of FIG. 7 is allowed.

On the contrary, in the case that step S1301 makes a negative determination, the inhibition flag is turned ON in step S1303. Accordingly, above-described step S701 makes a negative determination. As a result, the detecting process of the nick abnormality in the detecting element of the catalyst rear sensor 18 is inhibited.

As mentioned above, in the case that the intake air amount exceeds a predetermined amount, more specifically, exceeds a predetermined value (a second predetermined amount which is more than the first predetermined amount in the above condition (the condition a4)), the detecting process of the nick abnormality in the detecting element of the catalyst rear sensor 18 is inhibited. Accordingly, in the case that the nick abnormality is not generated in the detecting element of the catalyst rear sensor 18, even if the air-fuel ratio variation abnormality between the cylinders is generated, it is possible to prevent the nick abnormality generation from being erroneously detected (erroneously determined) in the detecting element of the catalyst rear sensor 18, due to the influence.

Next, a description will be given of a second embodiment according to the present invention. Since a structure of an engine to which the second embodiment is applied is substantially the same as the engine 1 mentioned above, a description thereof will be omitted. A description will be given below mainly of a difference from the first embodiment.

In the present second embodiment too, in order to prevent the nick abnormality from being erroneously detected in the detecting element of the catalyst rear sensor 18 in the case that the intake air amount is large, the detecting process is inhibited, as described in the first embodiment mentioned above. However, in the present second embodiment, a predetermined value for determining the inhibition is variable. Here, an inhibition determining predetermined value is calculated and set in accordance with the output fluctuation parameter X which is calculated as mentioned above.

The higher the air-fuel ratio variation degree between the cylinders is, the higher the tendency that the hydrogen is discharged to the exhaust passage is, and a degree that the catalyst rear sensor 18 has a lean output tendency is enhanced. Therefore, the catalyst rear sensor 18 tends to output an electric voltage indicating a lean side even with a reduced intake air amount as the air-fuel ratio variation degree between the cylinders becomes higher. Accordingly, a threshold value (a predetermined value) for determining whether or not the detecting process of the nick abnormality in the detecting element of the catalyst rear sensor 18 is inhibited is changed in accordance with the degree of the air-fuel ratio variation between the cylinders.

A description will be given below of an inhibiting process with respect to the detecting process of the nick abnormality in the detecting element 18a of the catalyst rear sensor 18 according to the second embodiment on the basis of a flow chart in FIG. 14. As can be easily understood from the following description, the ECU 20 takes charge of the functions of the value calculating unit and the like in the same manner as the ECU 20 according to the above-mentioned first embodiment, and further takes charge of a function of a predetermined amount calculating unit.

In step S1401, a predetermined value for inhibition is calculated on the basis of the output fluctuation parameter X, particularly on the basis of the parameter X which is most recently calculated. The output fluctuation parameter X can be calculated for this step, but, employs here the parameter X which is calculated in the course of the process of detecting the air-fuel ratio variation abnormality between the cylinders. Since the parameter X is not calculated in an initial state, the parameter X is set to zero, or an initial value which is previously set on the basis of experiments is used as the parameter X, in an initial stage. Note that, the output fluctuation parameter X which is held in the memory device when the engine 1 is stopped can be kept being stored in the ECU 20, and can be used at the time of starting the engine 1 thereafter.

Figure 15:
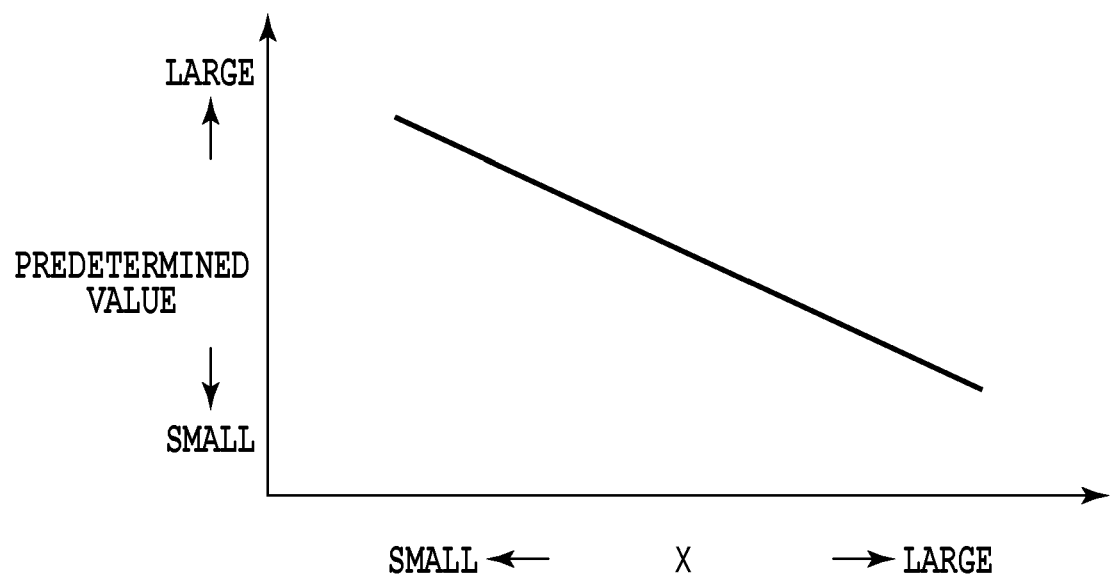
FIG. 15 is a graph showing a relationship between an output fluctuation parameter and a predetermined value for determining inhibition.

The predetermined value for inhibition and the parameter X have a relationship shown in FIG. 15, and the ECU 20 previously has data or calculating formula on the basis of the relationship, and calculates the predetermined value on the basis of them. As can be understood from FIG. 15, the predetermined value for inhibition and the parameter X have such a relationship that the greater the output fluctuation parameter X is, that is, the higher the degree of the air-fuel ratio variation between the cylinders is, the smaller the predetermined value for inhibition is. However, the predetermined value calculated in step S1401 is an air amount which is greater than the predetermined air amount of the above condition (the condition a4). Note that, in FIG. 15, the relationship between the predetermined value for inhibition and the parameter X changes linearly, but, can draw a predetermined curve.

Further, in step S1402, the predetermined value for inhibition calculated in step S1401 is compared with the intake air amount which is obtained on the basis of the output of the air flow meter 10. Further, in the case that step S1402 makes an affirmative determination since the intake air amount is equal to or less than the predetermined value, an inhibition flag is set to OFF in step S1403. As a result, the execution of the process of detecting the nick abnormality in the detecting element 18a of the catalyst rear sensor 18 is allowed (the affirmative determination in step S701). On the other hand, in the case that step S1402 makes a negative determination since the intake air amount exceeds the predetermined value, the inhibition flag is turned ON in step S1404. As a result, the process of detecting the nick abnormality in the detecting element 18a of the catalyst rear sensor 18 is inhibited (the negative determination in step S701).

Next, a description will be given of a third embodiment according to the present invention. Since a structure of an engine to which the third embodiment is applied is substantially the same as the engine 1 mentioned above, a description thereof will be omitted. A description will be given below mainly of a difference from the first embodiment.

In the present third embodiment too, in order to prevent the nick abnormality from being erroneously detected in the detecting element of the catalyst rear sensor 18 in the case that the intake air amount is large, the detecting process is inhibited, as described in the first embodiment mentioned above. On the other hand, in the case that the degree of the air-fuel ratio variation between the cylinders is not high to some degree, the erroneous detection of the nick abnormality in the detecting element of the catalyst rear sensor 18 is not generated or is hard to be generated even if the intake air amount is large. Accordingly, in the present third embodiment, the execution of the inhibiting process is selected in accordance with the degree of the air-fuel ratio variation between the cylinders. As a result, it is possible to enhance an execution frequency of the process of detecting the nick abnormality in the detecting element of the catalyst rear sensor 18.

Figure 16:
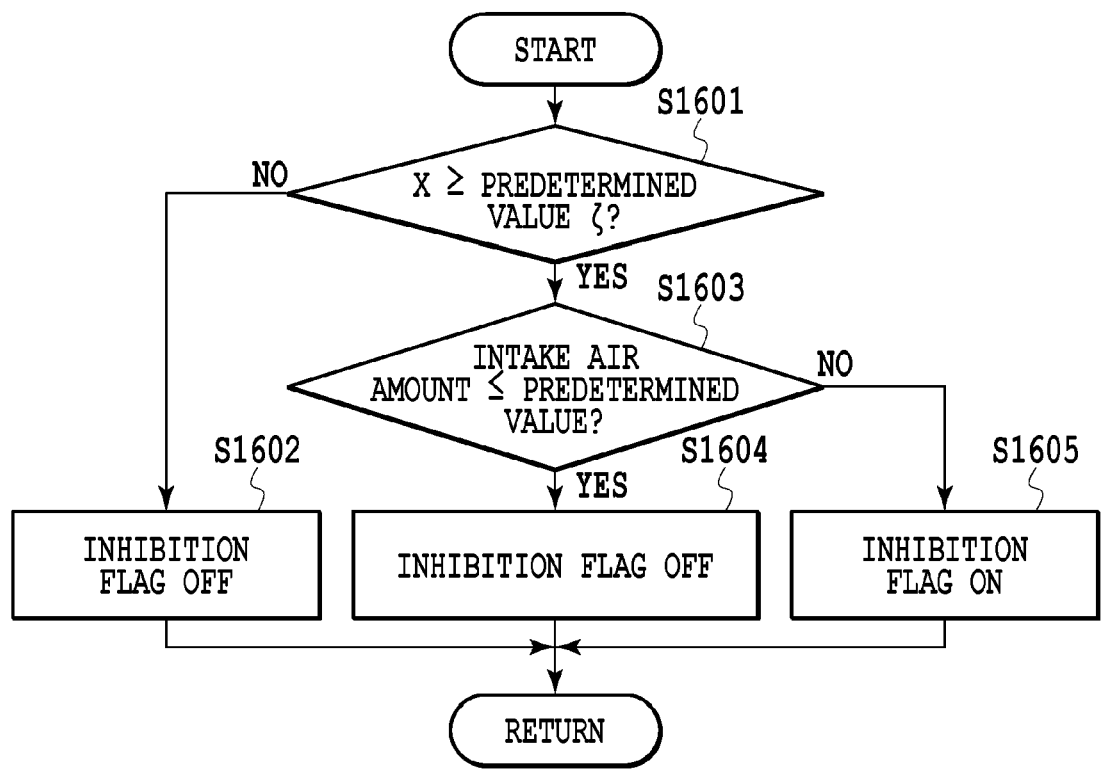
FIG. 16 is a flow chart of a process of inhibiting detection of a sensor nick abnormality in a third embodiment.

A description will be given below of an inhibiting process with respect to the detecting process of the nick abnormality in the detecting element 18a of the catalyst rear sensor 18 according to the third embodiment on the basis of a flow chart in FIG. 16. As can be easily understood from the following description, the ECU 20 takes charge of the functions of the value calculating unit and the like in the same manner as the ECU 20 according to the above-mentioned first embodiment, and further takes charge of a function of each of the variation level detecting unit and the second inhibiting unit.

Step S1601 determines whether or not the output fluctuation parameter X is equal to or more than a predetermined value $\zeta$. The predetermined value $\zeta$ is set as a threshold value for determining whether or not the air-fuel ratio variation degree between the cylinders is equal to or more than a predetermined degree, that is, a predetermined level. Here, as shown in FIG. 11, the predetermined value ζ is previously set as a value which is smaller than the predetermined value ε (step S1206) for determining the air-fuel ratio variation abnormality between the cylinders, on the basis of experiments. This is because there is a risk that the erroneous detection of the nick abnormality in the detecting element of the catalyst rear sensor 18 is generated due to the air-fuel ratio variation between the cylinders, even if it is not such the air-fuel ratio variation between the cylinders that is determined to be abnormal. In some engine, the predetermined value ζ may be the same as the predetermined value ε for determining the air-fuel ratio variation abnormality between the cylinders. However, the output fluctuation parameter X is set to zero in an initial state. Note that, the output fluctuation parameter X when the engine 1 may be stopped is stored and held in the ECU 20, and may be used thereafter at the time of starting the engine 1.

Since the air-fuel ratio variation degree between the cylinders does not reach a predetermined level in the case that step S1601 makes a negative determination, an inhibition flag is set to OFF in step S1602. Accordingly, the execution of the process of detecting the nick abnormality in the detecting element of the catalyst rear sensor 18 is allowed (the affirmative determination in step S701).

If step S1601 makes an affirmative determination, step S1603 determines whether or not the intake air amount is equal to or less than a predetermined value. Further, the inhibition flag is set to OFF or ON in step S1604 or S1605 in accordance with results of determination in step S1603. Since steps S1603 to S1605 are respectively the same as steps S1301 to S1303, a description thereof will be omitted.

As mentioned above, in the present third embodiment, the variation level detecting unit corresponds to step S1601. Further, since reaching step S1602 after the negative determination in step S1601 corresponds to the inhibition of the processes from step S1603 to S1605, it corresponds to the second inhibiting unit.

Figure 14:
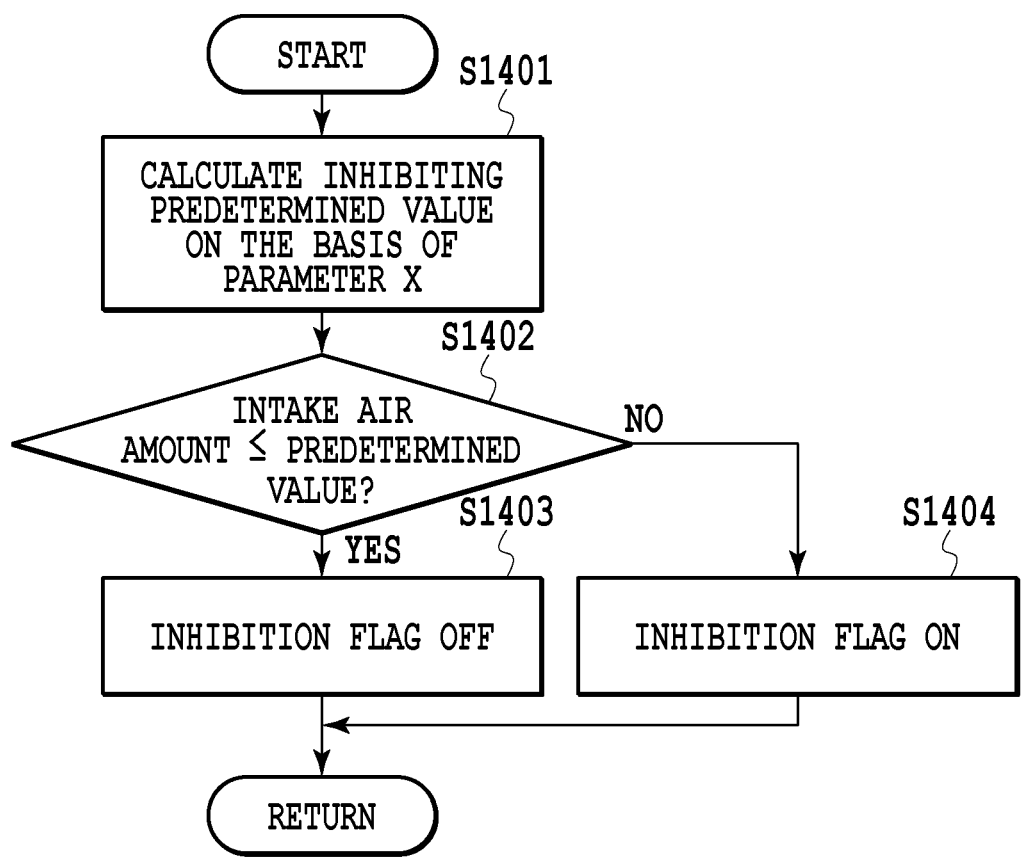
FIG. 14 is a flow chart of a process of inhibiting detection of a sensor nick abnormality in a second embodiment.

Note that, the predetermined value in step S1603 in the third embodiment may be variable as in the second embodiment, and can be set by being calculated on the basis of the output fluctuation parameter X (refer to step S1401 in FIG. 14, and FIG. 15). According to the configuration mentioned above, it is possible to more appropriately prevent the erroneous detection of the nick abnormality in the detecting element of the catalyst rear sensor 18.

In the described three embodiments according to the present invention, the catalyst rear sensor 18 is the oxygen sensor, but, may be the wide area air-fuel ratio sensor as with the catalyst front sensor 17. The wide area air-fuel ratio sensor can also generate the output which is biased to the lean side, in the case that the nick exists in the sensor. Therefore, the nick abnormality of the wide area air-fuel ratio sensor can be detected in the same manner as the process described on the basis of the flow chart in FIG. 7. On the other hand, the wide area air-fuel ratio sensor serving as the catalyst rear sensor 18 strongly tends to generate the output which is biased to the lean side in the case that the degree of the air-fuel ratio variation between the cylinders is high, and the intake air amount is large. Therefore, even in the case that the catalyst rear sensor 18 is the wide area air-fuel ratio sensor, the various processes mentioned above according to the first to third embodiments can be applied in the same manner.

The embodiments according to the present invention are not limited to the embodiments mentioned above. The present invention can include various modified examples, applied examples and equivalents, included in the concept of the present invention which is defined by claims.

What is claimed is:

1. An abnormality detecting device of an internal combustion engine comprising:
    a sensor nick abnormality detecting unit configured to detect a nick abnormality in a detecting element of a downstream side sensor which is provided in a downstream side of an exhaust gas purifying catalyst in an exhaust passage of an internal combustion engine having a plurality of cylinders and generates an output corresponding to an oxygen concentration in exhaust gas, on the basis of an output of the downstream side sensor, the sensor nick abnormality detecting unit detecting the nick abnormality in the detecting element of the downstream side sensor on the basis of a matter that a distribution of the output of the downstream side sensor is biased to an area in which the air-fuel ratio is leaner than a theoretical air-fuel ratio;
    an inhibiting unit configured to inhibit detection of the nick abnormality of the detecting element by the sensor nick abnormality detecting unit in the case that an intake air amount exceeds a predetermined amount;
    a value calculating unit configured to calculate a value indicating a degree of air-fuel ratio variation between the cylinders on the basis of an output of an upstream side air-fuel ratio sensor provided on an upstream side of the exhaust gas purifying catalyst;
    a variation level detecting unit configured to detect that the degree of the air-fuel ratio variation between the cylinders is equal to or more than a predetermined level by comparing the value calculated by the value calculating unit with a predetermined value; and
    a second inhibiting unit configured to inhibit an operation of the inhibiting unit in the case that the variation level detecting unit does not detect that the degree of the air-fuel ratio variation between the cylinders is equal to or more than the predetermined level.

2. The abnormality detecting device of an internal combustion engine according to claim 1, wherein the sensor nick abnormality detecting unit acquires an output voltage of the downstream side sensor a predetermined number of times, and determines a distribution of the output of the downstream side sensor on the basis of a number of times that the acquired output voltage is included in a predetermined voltage area.

3. The abnormality detecting device of an internal combustion engine according to claim 1, wherein the sensor nick abnormality detecting unit detects the nick abnormality of the detecting element of the downstream side sensor on the basis of the output of the downstream side sensor in the case that an air-fuel ratio feedback stoichiometric control is carried out.

4. The abnormality detecting device of an internal combustion engine according to claim 1, further comprising:
    a predetermined amount calculating unit configured to calculate the predetermined amount in the inhibiting unit on the basis of the value calculated by the value calculating unit.

5. The abnormality detecting device of an internal combustion engine according to claim 1, wherein
    the sensor nick abnormality detecting unit is configured to detect a nick abnormality in the detecting element of the downstream side sensor, on the basis of an output of the downstream side sensor in the case that an intake air amount is equal to or more than a first predetermined amount; and
    the first predetermined amount is less than the predetermined amount.

* * * * *